United States Patent
Brown et al.

(10) Patent No.: US 11,179,531 B2
(45) Date of Patent: Nov. 23, 2021

(54) APPARATUS, SYSTEMS, AND METHODS FOR ACCESSING THE AIRWAY WITH MEDICAL INSTRUMENTS WITHOUT INTERRUPTION OF ASSISTED RESPIRATION

(71) Applicant: Intermountain Intellectual Asset Management, LLC, Salt Lake City, UT (US)

(72) Inventors: Samuel Brown, Salt Lake City, UT (US); Troy Jesse Orr, Draper, UT (US)

(73) Assignee: Intermountain Intellectual Asset Management, LLC, Salt Lake City, UT (US)

(*) Notice: Subject to any disclaimer, the term of this patent is extended or adjusted under 35 U.S.C. 154(b) by 413 days.

(21) Appl. No.: 15/966,996

(22) Filed: Apr. 30, 2018

(65) Prior Publication Data

US 2018/0333553 A1 Nov. 22, 2018

Related U.S. Application Data

(63) Continuation of application No. 13/980,928, filed as application No. PCT/US2012/021814 on Jan. 19, 2012, now abandoned.
(Continued)

(51) Int. Cl.
*A61M 16/04* (2006.01)
*A61M 16/08* (2006.01)
(Continued)

(52) U.S. Cl.
CPC ..... *A61M 16/0488* (2013.01); *A61B 1/00154* (2013.01); *A61B 1/00165* (2013.01);
(Continued)

(58) Field of Classification Search
CPC .......... A61M 16/0488–0497; A61M 16/0633; A61M 16/08–0833; A61M 16/0078;
(Continued)

(56) References Cited

U.S. PATENT DOCUMENTS 4,506,665 A * 3/1985 Andrews ............... A61M 16/08
128/202.27
4,580,556 A * 4/1986 Kondur .................. A61B 1/267
128/206.28
(Continued)

FOREIGN PATENT DOCUMENTS

WO 2012100016 7/2012

OTHER PUBLICATIONS

International Search Report (ISR) and Written Opinion (WO) dated May 23, 2012 for international application PCT/US2012/021814.
(Continued)

*Primary Examiner* — Elliot S Ruddie
(74) *Attorney, Agent, or Firm* — Stoel Rives LLP; Jordan B. Olsen

(57) ABSTRACT

Systems for use in assisted respiration can permit insertion of one or more elongated medical instruments into the proximal and/or distal airway of a patient during administration of assisted respiration, which may, in some instances, proceed with a patient awake or only minimally sedated. In some systems, a bite block is coupled with a mask and is movable relative to the mask such that the system is capable of accommodating differing patient anatomies.

11 Claims, 23 Drawing Sheets

Related U.S. Application Data

(60) Provisional application No. 61/435,301, filed on Jan. 22, 2011.

(51) Int. Cl.
*A61M 16/06* (2006.01)
*A61B 1/00* (2006.01)
*A61B 1/267* (2006.01)
*A61M 16/00* (2006.01)
*A61M 16/20* (2006.01)

(52) U.S. Cl.
CPC ....... *A61B 1/2676* (2013.01); *A61M 16/0078* (2013.01); *A61M 16/0493* (2014.02); *A61M 16/0495* (2014.02); *A61M 16/06* (2013.01); *A61M 16/0633* (2014.02); *A61M 16/0816* (2013.01); *A61M 16/0825* (2014.02); *A61M 16/0833* (2014.02); *A61M 16/0463* (2013.01); *A61M 16/0683* (2013.01); *A61M 16/208* (2013.01); *A61M 2210/0625* (2013.01)

(58) Field of Classification Search
CPC .............. A61M 16/06; A61M 16/0463; A61M 16/0683; A61M 16/208; A61M 2210/0625; A61M 16/20; A61B 1/00147–00154; A61B 1/00165; A61B 1/00052; A61B 1/267–2676; A61B 5/0084
USPC .................. 600/114, 153–154, 156, 158–159
See application file for complete search history.

(56) References Cited

U.S. PATENT DOCUMENTS

| | | | |
|---|---|---|---|
| 4,848,331 A | | 7/1989 | Northway-Meyer |
| 5,676,133 A | * | 10/1997 | Hickle ................. A61M 16/00 128/202.27 |
| 5,694,929 A | | 12/1997 | Christopher |
| 6,257,236 B1 | | 7/2001 | Dutkiewicz |
| 6,568,388 B2 | | 5/2003 | Christopher |
| 6,792,943 B2 | | 9/2004 | Kumar et al. |
| 7,473,219 B1 | * | 1/2009 | Glenn ................ A61B 1/00068 600/114 |
| 2002/0023649 A1 | | 2/2002 | Gunaratnam et al. |
| 2005/0028811 A1 | * | 2/2005 | Nelson .................. A61M 16/06 128/200.11 |
| 2005/0139220 A1 | | 6/2005 | Christopher |
| 2006/0054168 A1 | | 3/2006 | Yu |
| 2008/0006270 A1 | | 1/2008 | Gershman et al. |
| 2009/0235932 A1 | * | 9/2009 | Nashed ............. A61M 16/0816 128/203.29 |
| 2011/0197892 A1 | * | 8/2011 | Koledin ............ A61M 16/0833 128/205.24 |

OTHER PUBLICATIONS

Janis—Are you Ready to Open It?, Biomedical Srl, Firenze, Italy http://www.biomedical-srl.com/wp-content/uploads/2012/08/JANUS-eng-2014-a4.pdf.

Brown, et al., Final Office Action dated Jul. 14, 2016 for U.S. Appl. No. 13/980,928.

Brown, et al., Non-Final Office Action dated Jun. 2, 2017 for U.S. Appl. No. 13/980,928.

Brown, et al., Non-Final Office Action dated Oct. 1, 2015 for U.S. Appl. No. 13/980,928.

Brown, et al., Office Action dated Dec. 28, 2017 for U.S. Appl. No. 13/980,928.

* cited by examiner

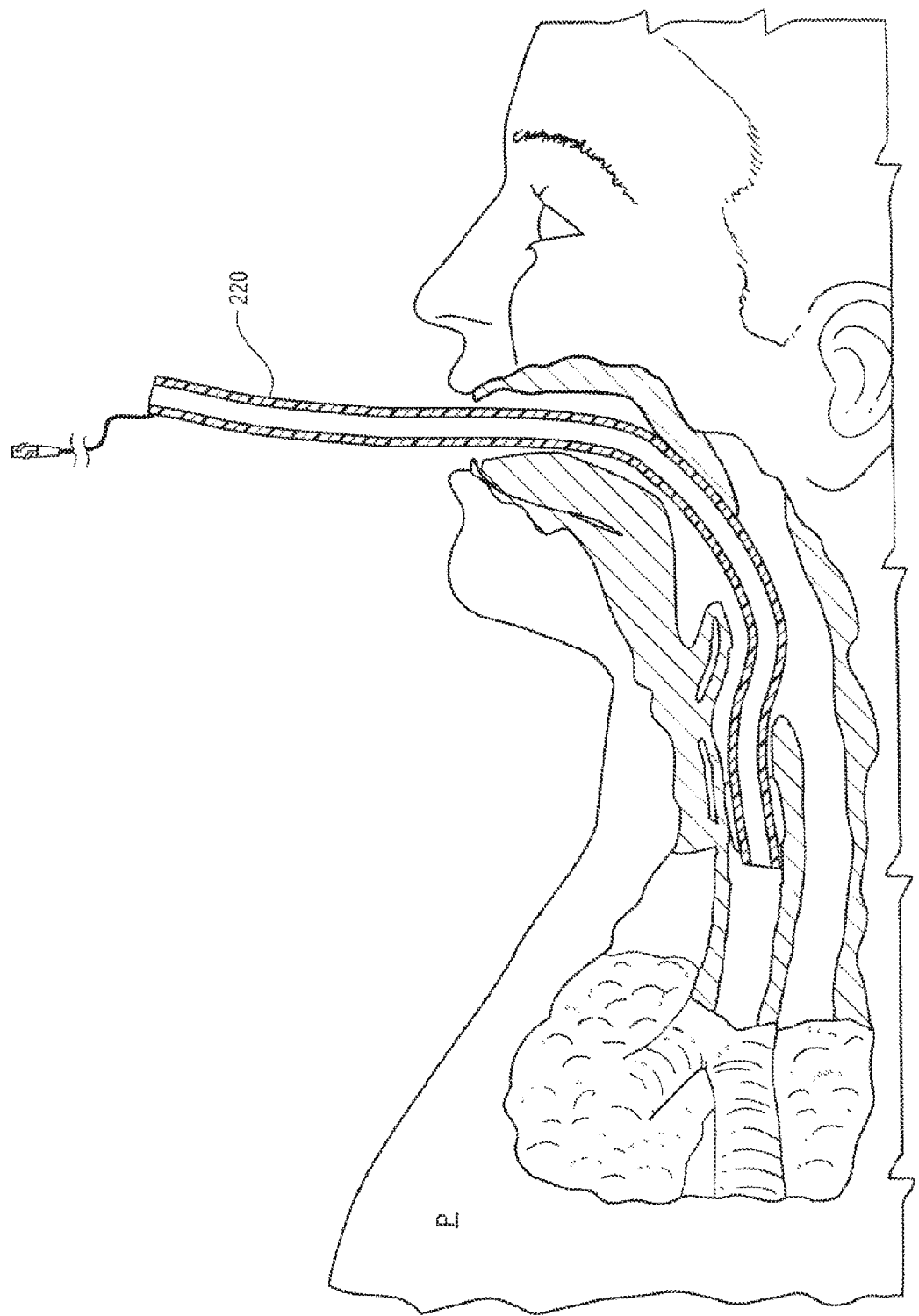

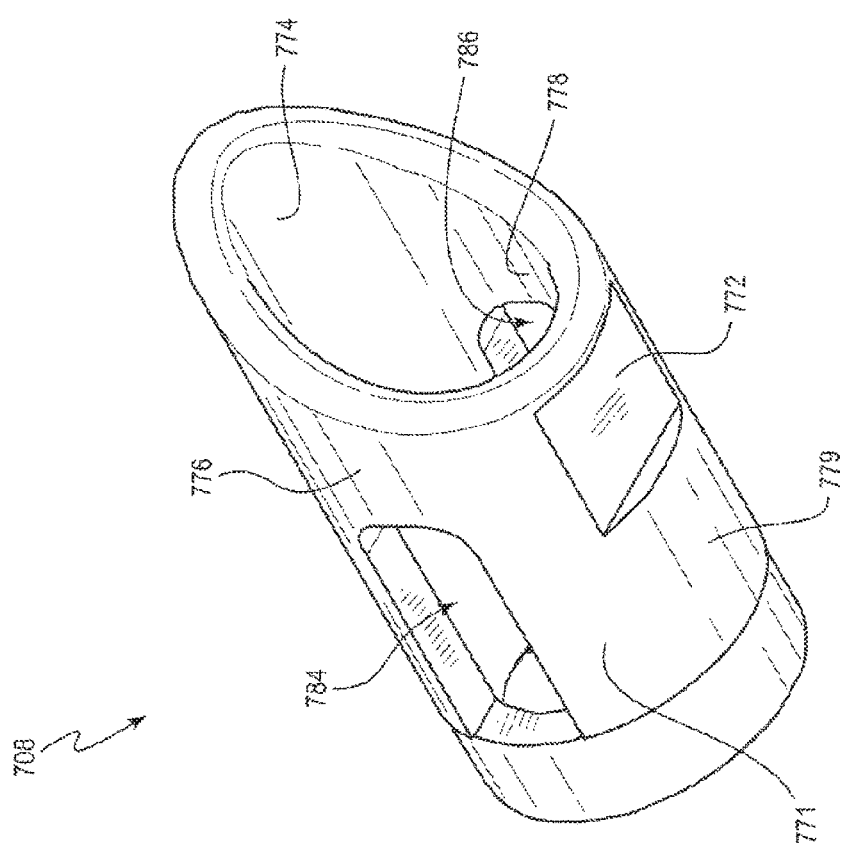

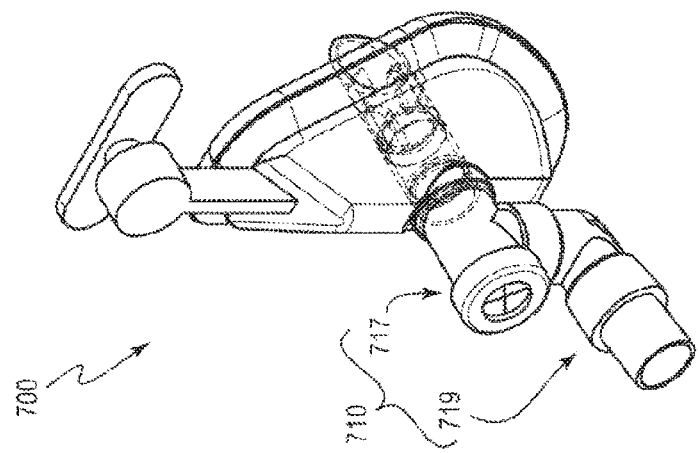
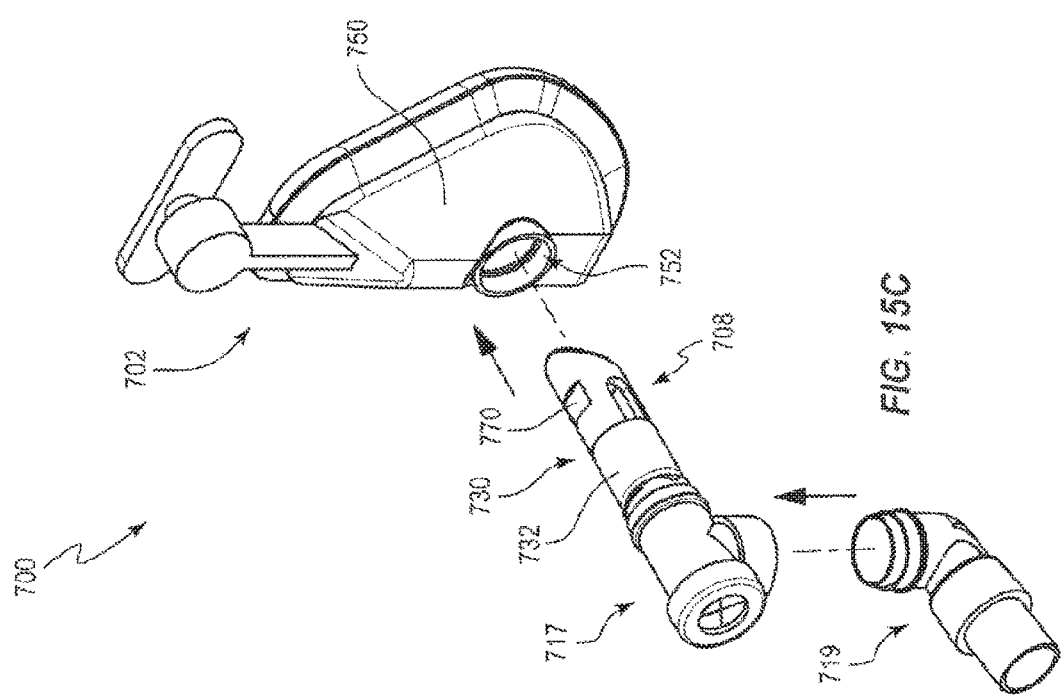

APPARATUS, SYSTEMS, AND METHODS FOR ACCESSING THE AIRWAY WITH MEDICAL INSTRUMENTS WITHOUT INTERRUPTION OF ASSISTED RESPIRATION

CROSS-REFERENCE TO RELATED APPLICATIONS

This patent application is a continuation of U.S. patent application Ser. No. 13/980,928, entitled APPARATUS, SYSTEMS, AND METHODS FOR ACCESSING THE AIRWAY WITH MEDICAL INSTRUMENTS WITHOUT INTERRUPTION OF ASSISTED RESPIRATION, filed on Jul. 22, 2013, which is the U.S. National Stage filing under 35 U.S.C. 371 of International Patent Application No. PCT/US2012/021814, entitled APPARATUS, SYSTEMS, AND METHODS FOR ACCESSING THE AIRWAY WITH MEDICAL INSTRUMENTS WITHOUT INTERRUPTION OF ASSISTED RESPIRATION, filed on Jan. 19, 2012, which claims priority to U.S. Provisional Patent Application No. 61/435,301 entitled APPARATUS, SYSTEMS, AND METHODS FOR ACCESSING THE AIRWAY WITH MEDICAL INSTRUMENTS WITHOUT INTERRUPTION OF ASSISTED RESPIRATION, filed on Jan. 22, 2011, each of which is incorporated herein by reference in its entirety.

TECHNICAL FIELD

The present disclosure relates generally to masks used for assisted respiration.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIGS. 6A-6E are cross-sectional views of the system of FIG. 1 coupled with a patient that depict various stages of an intubation process facilitated by use of a fiberoptic videoscope or other elongated medical instrument;

FIG. 14 is a rear perspective view of another embodiment of a bite block; and

FIGS. 15A-15D are perspective views of a process for augmenting an adapter so as to have instrument insertion capabilities.

DETAILED DESCRIPTION

Figure 1:
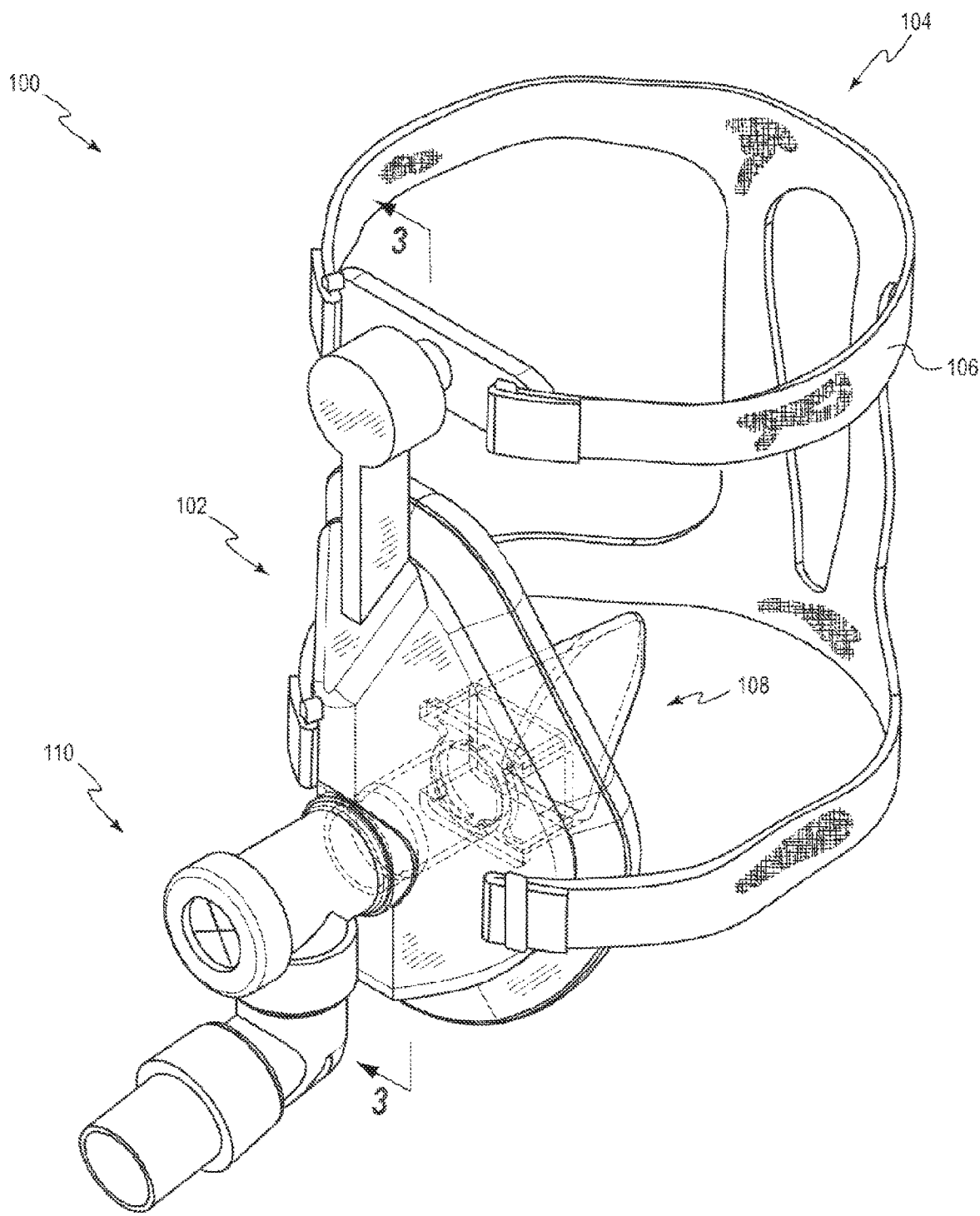
FIG. 1 is a perspective view of an embodiment of a system that is configured for use in assisted respiration and in intubating a patient.

Various embodiments of systems disclosed herein can be used in procedures that access the airway of a patient, such as bronchoscopy or fiberoptic tracheal intubation, without disrupting administration of assisted respiration to the patient, such as the administration of noninvasive positive pressure ventilation (NIPPV). Certain systems can include masks through which oxygen, air, or a combination of those gases, whether pressurized or unpressurized, can be administered. In some embodiments, a bite block that is coupled to a mask can be readily adjusted relative to the mask and inserted into the mouth of a patient such that the bite block can accommodate the specific anatomy of the patient. In other or further embodiments, the bite block can include features that can aid in advancing instruments for bronchoscopy and/or fiberoptic tracheal intubation into the airway of a patient.

Certain prior art procedures for emergency situations involving patients who have compromised or arrested breathing are known. In some instances, such patients may suffer from severe respiratory failure and/or cardiopulmonary arrest. In some procedures, an oral airway may first be inserted into the patient's mouth. A face mask may then be placed over the patient's mouth and nose. The face mask (e.g., a bag valve mask) may be connected to an inflatable bag to maintain at least minimal oxygen flow to the lungs in the short term. This particular process of artificial ventilation is sometimes referred to as "bagging" the patient, and may be suitable for initially stabilizing the patient. In order to support the patient's respiration during cardiopulmonary resuscitation, and to prevent aspiration of stomach contents, an endotracheal tube may be placed into the trachea. Longer-term care usually involves continued artificial ventilation and attaching the patient to a ventilator (e.g., by means of the endotracheal tube). Prior art techniques are only of use in unconscious patients or in patients unable to respire without assistance; they would not be tolerated in awake or semi-conscious patients who are at least partially respiring without assistance. In awake or semi-conscious patients, the transition from non-invasive assisted respiration to invasive (e.g., via endotracheal tube) is quite dangerous. Current techniques require induction of a comatose state and/or chemical paralysis and at least temporary separation from the oxygen source, which techniques may be associated with profound decrease in blood oxygen levels or blood pressure, or even cardiopulmonary arrest.

For example, a conventional approach to making a transition to an endotracheal tube involves induction of a comatose state with or without chemical paralysis, discontinuing respiration, and completely removing the mask and oral airway to expose the mouth. The physician then inserts a rigid laryngoscope blade into the patient's mouth and then inserts the endotracheal tube through the patient's mouth and upper airway and into the trachea in a conventional manner. The rigid laryngoscope blade is inserted into the mouth and advanced through the upper airway with an appropriate amount of force to distort the naturally curved airway so that the glottis is in straight alignment for direct visualization by the operator.

If the patient suffers from cardiopulmonary arrest, cardiac chest compressions are generally interrupted during this time because energy transmission from the vigorous cardiac chest compressions can cause an uncontrolled bouncing movement of the head and neck. Such movement of the head and neck can impair controlled manipulation of the laryngoscope for visualization and tube placement. Moreover, uncontrolled movement of the laryngoscope blade during forceful manipulation of the upper airway tissues can result in severe or life-threatening injury.

Endotracheal intubation with the rigid laryngoscope blade may require a significant amount of time, even if the patient is motionless. The procedure can be more difficult if the patient is less than completely cooperative and relaxed, if the patient's airway has suffered trauma, and/or if the tongue has fallen back to close the airway. The patient is generally not breathing during this time, or may not be breathing sufficiently to maintain adequate blood oxygen levels, particularly in situations of cardiac arrest. If the transition process takes more than several seconds, the physician may be forced to temporarily abandon the effort and return to resuscitation by reinserting the oral airway and replacing the face mask, and resuming cardiac chest compressions. The transition process may be repeated several times before the endotracheal tube is successfully inserted. In addition, the speed with which the transition process must be completed increases the chances of practitioner mistakes, such as unintended injury to the patient during the intubation procedure. Irreversible damage to vital organs such as the brain and heart can occur after about 30 seconds of interruption of artificial ventilation, and in an even shorter time in the absence of cardiac chest compressions.

Endotracheal tubes may also be used in emergency situations that have not yet resulted in cardiopulmonary arrest, such as to ventilate patients suffering severe respiratory failure who may be conscious or semi-conscious. A conventional approach can require a patient to lie still, unconscious and/or paralyzed, while the physician inserts a rigid laryngoscope blade into the patient's mouth and trachea. Delivery of ventilation and/or oxygen is interrupted during this period. The endotracheal tube is then inserted into the trachea while the laryngoscope blade keeps the patient's airway open. Profound decreases in blood oxygen or arterial blood pressure, and even cardiopulmonary arrest, can complicate the process of endotracheal intubation because of the usual requirement to sedate, temporarily cease assisted ventilation, and possibly paralyze the patient.

Certain embodiments disclosed herein can address, ameliorate, resolve, and/or eliminate one or more of the shortcomings of prior art devices and procedures, such as those just described. For example, some embodiments permit fiberoptic bronchoscopy or fiberoptic tracheal intubation in to proceed while a patient is receiving NIPPV and/or while the patient is awake or minimally sedated. In particular, certain embodiments could substantially decrease risk associated with transition to invasive assisted respiration by allowing the procedure to occur while the patient remains awake or minimally sedated and at least partly contributing to his/her own respiration. In some embodiments, a system includes a bite block that is coupled with a face mask in such a manner that a position of the bite block can be readily adjusted relative to the mask, and thus the system can be readily adjusted to conform to the anatomy of any particular patient. The bite block can be used to open the mouth of a patient to provide rapid access to the patient's airway. For example, in some embodiments, the bite block is positioned within the oral cavity so as to maintain the mouth in an open position and may be quickly positioned in the patient so that little preparation time is used in order to secure the mask to the patient, thereby providing assisted respiration to the patience as well as access to the patient's airway for the insertion of various instruments. Other features and advantages of embodiments discussed herein will be evident from the present disclosure.

The term "couple" (and any derivatives thereof) is a broad term used herein in its ordinary sense. The term is sufficiently broad to cover instances of both direct coupling, in which there is direct contact between coupled components, and indirect coupling, in which contact between the coupled components is not necessarily present and yet one or more positions of and/or movements of a first component relative to a second component are constrained, such as may be due to one or more intermediate components that are connected to each of the first and second components.

FIG. 1 illustrates an embodiment of a system 100 that can be used in assisted respiration and to provide access to the airway of a patient. The system 100 includes a mask 102 that can be configured for placement over the mouth and/or nose of a patient (see, e.g., FIG. 6A). The system 100 can further comprise an attachment assembly 104 by which the mask 102 can be coupled to the head and face of a patient. In the illustrated embodiment, the attachment assembly 104 comprises a plurality of flexible straps or bands 106, which may be stretchable or resiliently deformable. Any suitable arrangement for the attachment assembly 104 is possible.

The system 100 further includes a bite block 108 that can be configured for placement in the oral cavity of a patient. The bite block 108 can be coupled with the mask 102 and can be movable relative thereto so as to permit the system 100 to accommodate a variety of different patient anatomies. The system 100 also includes an adapter 110 that can be coupled with the mask 102. The adapter 110 can be configured to provide oxygen and/or other gases (e.g., air) to the mask 102. The adapter 110 can further be configured to assist in, or permit, the insertion of one or more instruments in to the airway of a patient. For example, the adapter 110 can be configured to permit the passage of a fiberscope or other instrument into the airway of a patient, and may further permit an endotracheal tube to be passed over a fiberscope into the patient. The adapter 110 can permit the insertion of such instruments while simultaneously providing oxygen and/or other gases to the patient. In some embodiments, the assisted respiration source adapter 110 is coupled with the bite block 108.

Figure 2:
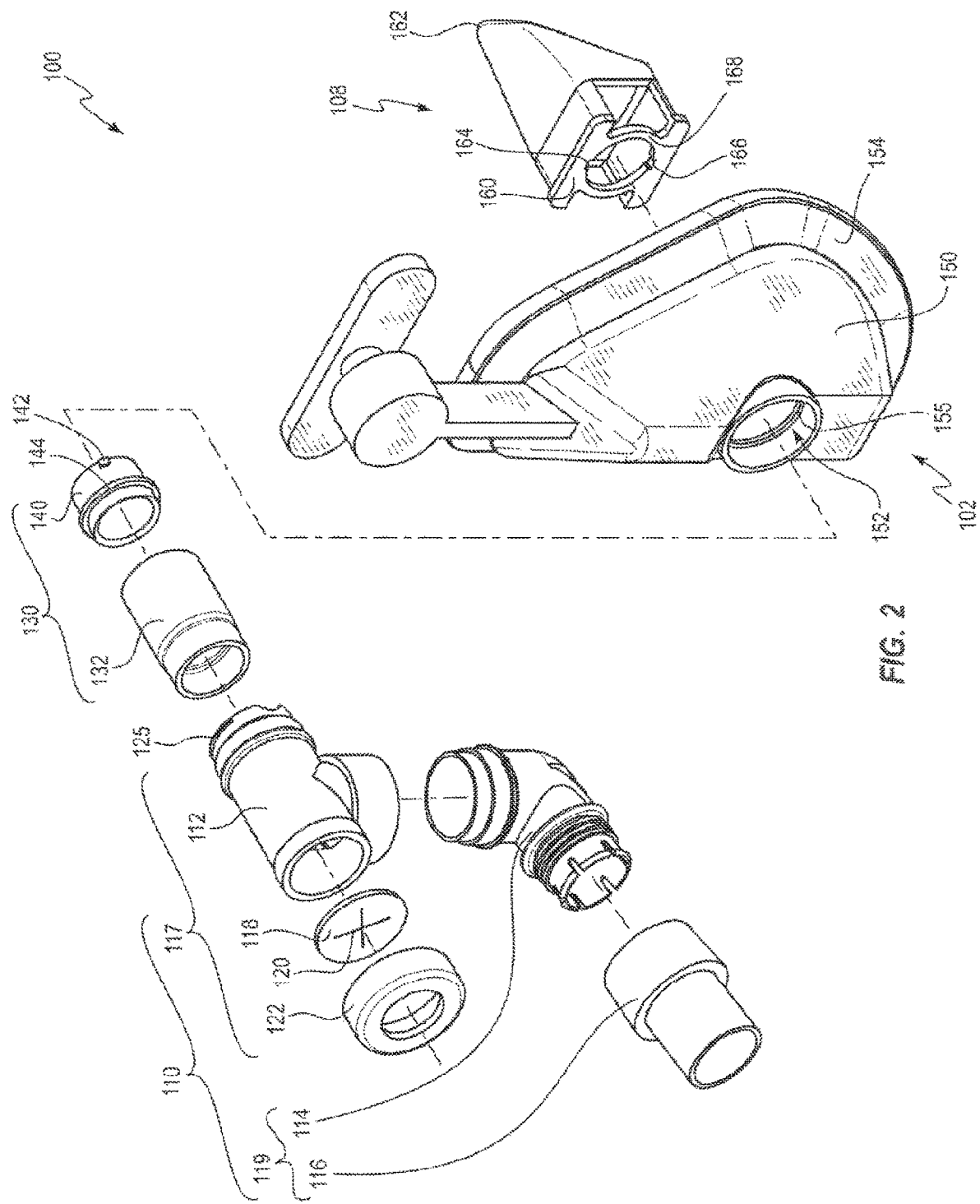
FIG. 2 is an exploded perspective view of the system of FIG. 1, but without an embodiment of a strap that is shown in FIG. 1.
Figure 3:
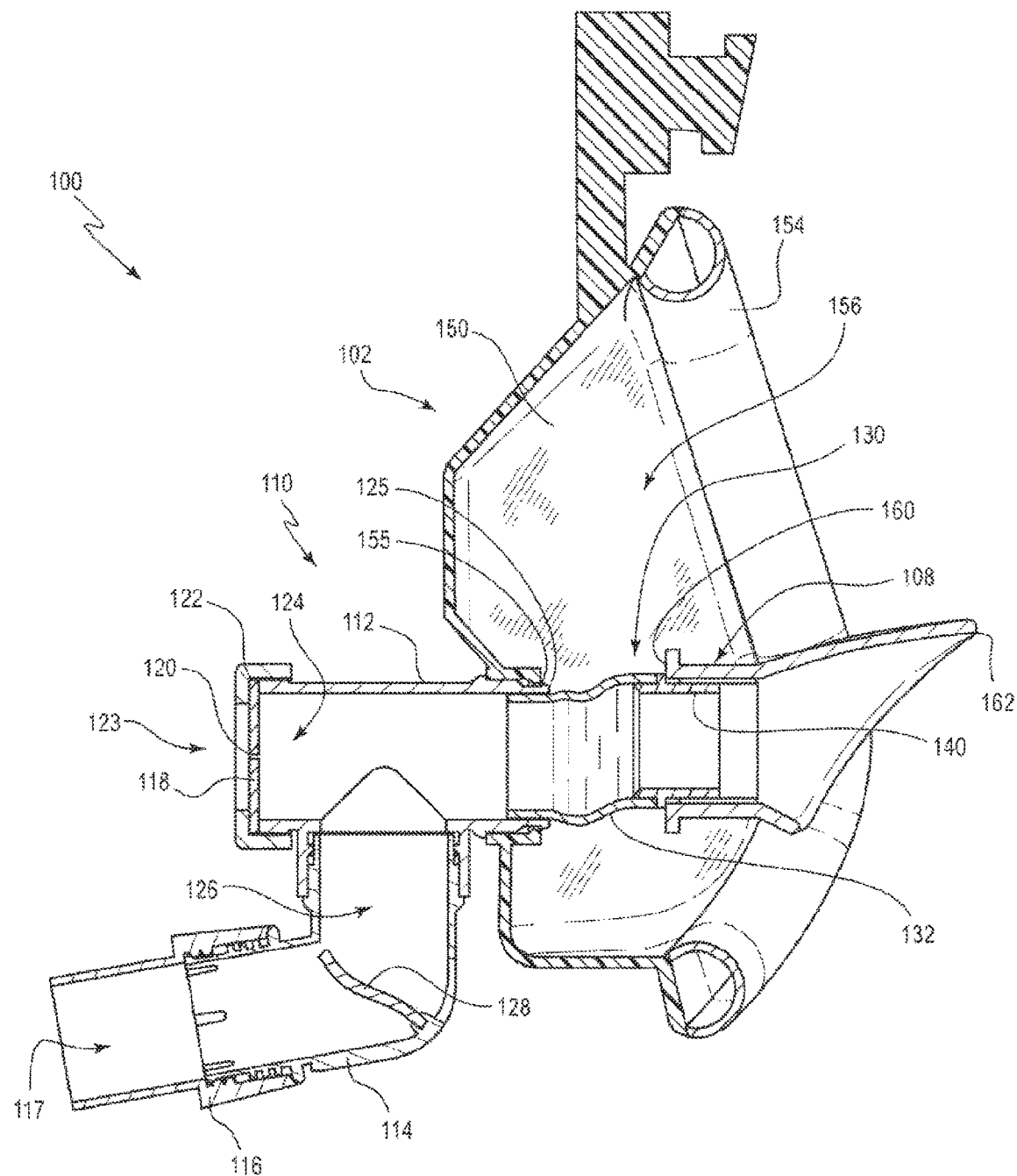
FIG. 3 is a cross-sectional view of the system of FIG. 1 taken along the view line 3-3 in FIG. 1.

FIGS. 2 and 3 depict additional views of the system 100, absent the attachment assembly 104. In the illustrated embodiment, the adapter 110 comprises two separate assemblies 117, 119. An insertion assembly 117, which may also be referred to as an insertion portal or insertion adapter, is configured to allow the insertion of various devices into the airway of a patient through the mask 102. An assisted respiration source assembly 119, which may also be referred to as an assisted respiration source adapter, is configured to be coupled with an assisted respiration source 205 (see FIG. 6A) so as to receive oxygen and/or other gases (e.g., air) and direct them to the mask 102. The adapter 110, as a composite of the assemblies 117, thus itself may be referred to as an insertion assembly, insertion portal, insertion adapter, assisted respiration source assembly, and/or assisted respiration source adapter.

In the illustrated embodiment, the insertion assembly 117 comprises a housing 112 that is shaped substantially as a T-joint. As shown in FIG. 3, the housing 112 defines an insertion channel or passageway 124 through which instruments can be passed into the airway of a patient while the mask 102 is in place. The housing 112 further defines a portion of a respiration channel or passageway 126 through which gases can pass from an assisted respiration source 205 (see FIG. 6A). The insertion passageway 124 is in fluid communication with the respiration passageway 126, such that the gases from the assisted respiration source 205 also are permitted to pass through the insertion passageway 124 and into the mask 102.

With reference again to both FIGS. 2 and 3, the insertion assembly 117 can include a valve 118 of any suitable variety. In the illustrated embodiment, the valve 118 comprises a septum that includes one or more slits 120. The valve 118 can be held against an open end of the housing 112 via a collar 122. As shown in FIG. 3, the valved end of the housing 112 can define a port 123 through which instruments may be inserted.

As shown in FIGS. 2 and 3, the assisted respiration source assembly 119 can comprise diverter 114, which can be configured to direct a flow path of gases from an assisted respiration source along a path that is angled away from or otherwise does not interfere with instruments that may be inserted through the port 123 of the insertion assembly 117. In the illustrated embodiment, the diverter 114 comprises an elbow joint. A first end of the diverter 114 can comprise a connection interface that is configured to couple with the housing 112 in any suitable manner. A second end of the diverter 114 may comprise a connection interface that is configured to couple with an assisted respiration source 205 in any suitable manner. In the illustrated embodiment, the second end of the diverter 114 is coupled with a connector 116, which defines the suitable interface for connection to an assisted respiration source 205.

The assisted respiration source assembly 119 can comprise a valve 128 that is configured to control a direction of gas flow through the assembly 119. In the illustrated embodiment, the valve 128 comprises a one-way valve, such that gas flow is preferentially permitted into the mask. Any suitable arrangement for the assisted respiration source assembly 119 is possible. For example, some assisted respiration source assemblies 119 that are directly connected to masks for NIPPV applications are known in the art, and can be suitable for use in the adapter 110.

In the illustrated embodiment, the insertion assembly 110 is coupled with a connection assembly 130, which is coupled with the bite block 108. The connection assembly 130 can be configured to secure the bite block 108 to the mask 102, yet permit the bite block 108 to move relative to the mask 102, as discussed further below. In the illustrated embodiment, the connection assembly 130 comprises a conduit 132 and a connector sleeve 140. The conduit 132 can comprise any suitable material and may be rigid, semi-rigid, or flexible. In the illustrated embodiment, the conduit 132 comprises a flexible material that is resiliently deformable. The conduit 132 can define a passage through which gases can be delivered from the adapter 110 to the bite block 108. In the illustrated embodiment, a sidewall of the conduit 132 is substantially solid or uninterrupted such that the gases are delivered directly to the bite block 108 without leakage into the mask 102 through the conduit. Other arrangements of the conduit 132 are also possible. For example, in some embodiments, the conduit 132 can include one or more openings in its sidewall.

In other embodiments, the connection assembly 130 may comprise other suitable attachment devices to secure the bite block 108 to the mask 102. For example, in some embodiments, the connection assembly 130 includes one or more tethers or leashes in place of the conduit 132.

The connector sleeve 140 comprises a plurality of stops 144, 142 that are configured to maintain the bite block 108 coupled therewith in a movable fashion. In the illustrated embodiment, a forward stop 144 comprises an outwardly extending lip or flange that encircles the connector sleeve 140. A rearward stop 142 comprises two outwardly extending protrusions (only one of which is shown) that can act as a keying system for coupling the bite block 108 to the connector sleeve 140 and maintaining the bite block 108 in the coupled state.

The bite block 108 can include a coupling ring 168 that is configured to cooperate with the connector sleeve 140 to couple the bite block 108 with the connector sleeve 140 and also to permit the bite block 108 to move in a constrained manner when the connector sleeve 140 and the bite block 108 are coupled with each other. The coupling ring 168 defines an upper notch 164 and a lower notch 166 that are sized to permit the outwardly extending rearward stops 142 to pass through. In order to couple the bite block 108 with the connector sleeve 140, the notches 164, 166 are aligned with the stops 142, the bite block 108 is advanced over the connector sleeve 140, and the bite block 108 is then rotated to lock the bite block 108 in place. The bite block 108 thus may be rotatable relative to the connector sleeve 140 about a central axis of the connector sleeve 140. The bite block 108 can remain coupled with the connector sleeve 140 over a large rotational range, although the bite block 108 can be decoupled from the connector sleeve 140 by again aligning the notches 164, 166 with the stops 142 and retracting the bite block 108 from the connector sleeve 140.

In other embodiments, the bite block 108 may be permanently attached to the connector sleeve 140 and may be fixed relative to at least that portion to which it is connected. For example, the bite block 108 may be integrally formed with the connector sleeve 140. In still other embodiments, the connector sleeve 140 may be eliminated and the bite block 108 may be directly connected to the conduit 132 and/or may be integrally formed therewith. Other suitable arrangements for the conduit 132, the connector sleeve 140, and/or the bite block 108 are also possible.

The mask 102 can include a structural shell 150. In some embodiments, the mask 102 further includes a pad or cushion 154 that extends about a periphery of the shell 150 and is configured to interface with the face of a patient. The shell 150 can define an adapter opening 152 through which instruments may be passed through the mask 102 and into the airway of a patient. The adapter 110 can be attached to the mask 102 at the adapter opening 152. Any suitable arrangement for coupling the adapter 110 to the mask 102 is contemplated. In the illustrated embodiment, the housing 112 of the adapter 110 includes a connector 125 of any suitable variety, such as a deformable snap or clip, which interacts with an inwardly projecting rim 155 that is defined about the adapter opening 152.

Any suitable method may be used to assemble the system 100. As depicted in FIG. 2 via a broken line, in the illustrated embodiment, the connection assembly 130 is sized so as to be inserted through the adapter opening 152 of the shell 150. The connection assembly 130 thus can be inserted through the adapter opening 152 and the housing 112 of the adapter 110 can be connected to the shell 150. Thereafter, the bite block 108 can be attached to the connector sleeve 140 in a manner such as discussed above. In other embodiments, the connection assembly 130 may be coupled directly to the shell 150. In still other embodiments, the connection assembly 130 can be connected to the adapter 110 after the adapter 110 has been coupled to the shell 150.

With reference to FIG. 3, the mask 102 can define a cavity 156 that is sized to receive at least a portion of the nose and the lips of a patient therein. The cavity 156 can extend to the bottom edge of the cushion 154, which as previously mentioned, can be configured to encompass at least a portion of the nose and the mouth of a patient. The bite block 108 can be configured to move relative to the mask 102 so as to be able to accommodate differing patient anatomies, as discussed further hereafter. In some embodiments, a distal end 162 of the bite block 108 can be positioned at an exterior of the cavity 156 defined by the mask 102. The distal end 162 may be positioned deep within the oral cavity of the patient, but spaced from the pharynx, as discussed further below.

In some embodiments, a proximal end 160 of the bite block 108 is positioned at an interior of the cavity 156 when the system 100 is in a resting, initial, or unused state. When the system 100 is coupled to a patient, the bite block 108 can be adjusted to fit in the mouth of the patient and thus can be moved relative to the mask 102. The proximal end 160 of the bite block 108 may remain within the cavity 156 of the mask 102 throughout the adjustment, and can remain spaced from the adapter opening 152 of the shell 150. The flexible conduit 132 can be bent, deformed, or otherwise displaced to permit the adjustment of the bite block 108.

Figure 4A:
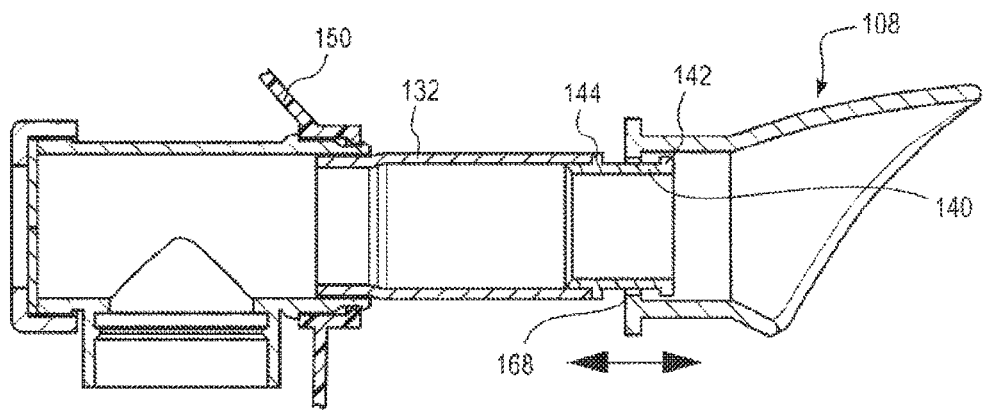
FIGS. 4A-4C are cross-sectional views of a portion of the system of FIG. 1 showing an embodiment of a bite block in a variety of different positions.
Figure 4B:
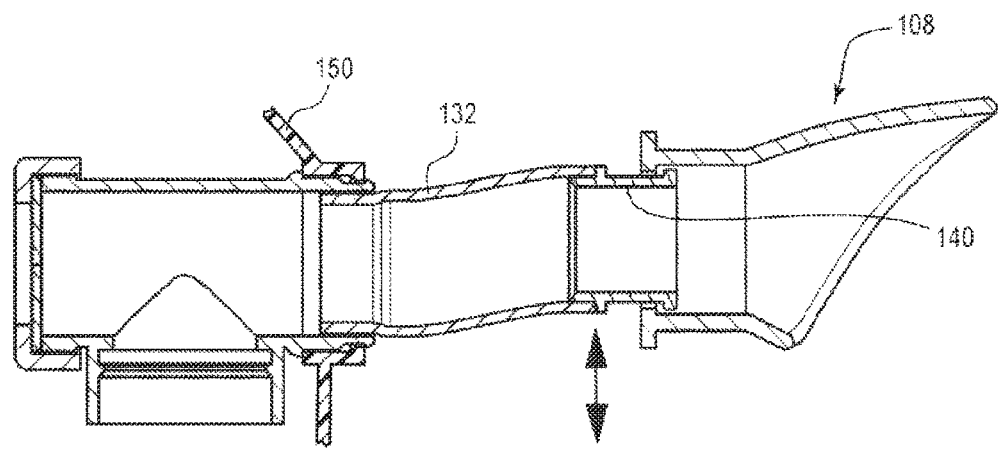
Figure 4C:
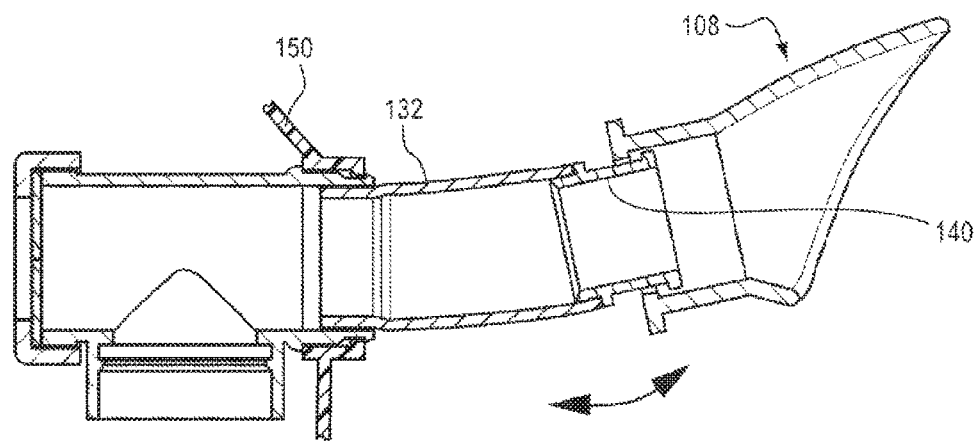

FIGS. 4A-4C illustrate various adjustments or movements of the bite block 108 that can be made relative to the shell 150 of the mask 102, which can allow the system 100 to be adjusted or conform to a particular patient. With reference to FIG. 4A, the bite block 108 can translate toward or away from the shell 150 along the connector sleeve 140, as depicted by the double-headed arrow. The translational movement can be limited by interaction between the coupling ring 168 of the bite block 108 and the forward and rearward stops 144, 142. Although not depicted by an arrow, the bite block 108 likewise can rotate relative to the connector sleeve 140 about a longitudinal central axis, which may be common to the bite block 108 and the connector sleeve 140.

As shown in FIG. 4B, the bite block 108 likewise can be permitted to move laterally (e.g., up, down, side-to-side, etc.) relative to the shell 150, as depicted by the double-headed arrow. The flexible conduit 132 can be deformed so as to permit such movement.

As shown in FIG. 4C, the bite block 108 can per permitted to rotate relative to the shell 150 about a variety of axes other than the longitudinal central axis defined by the connector sleeve 140. The flexible conduit 132 can be deformed so as to permit such movement. Accordingly, the bite block 108 can have multiple degrees of freedom of movement relative to the shell 150. Other suitable arrangements that allow for movement of the bite block 108 are also possible, as discussed further below.

FIGS. 5A-5D illustrate an embodiment of the bite block 108, which can include features that assist in orientation and/or advancement of medical instruments into the airway of a patient. The bite block 108 can include an upper bite plate 170 and a lower bite plate 172 that are shaped and sized to contact one or more upper teeth and one or more lower teeth, respectively. A patient thus can bite against the upper and lower bite plates 170, 172 so as to maintain the bite block 108 within the mouth of the patient. In the illustrated embodiment, each of the upper and lower bite plates 170, 172 is substantially rectangular and planar, although other suitable configurations are also possible.

The upper and lower bite plates 170, 172 cooperate to define a forward end of passageway 173 through which an elongated medical instrument may pass. As further discussed below, the bite block 108 can be particularly helpful in positioning a fiberscope that is advanced through the passageway 173. The passageway 173 can be sufficiently large to permit an endotracheal tube to be passed over such a fiberscope through the passageway 173.

The bite block 108 can include a guide plate 174 that extends rearwardly from the upper bite plate 170. An upper surface of the guide plate 174 can be contoured so as to be able to fit against or near a roof of a mouth of a patient. For example, the upper surface can be convexly rounded (see FIG. 5D), although other configurations are also possible. A lower surface of the guide plate 174 can be concavely rounded. In the illustrated embodiment, the guide plate 174 angles upwardly from the upper bite plate 170.

The guide plate 174 can be sized so as to be maintained within the oral cavity of a patient when the patient bites on the bite plates 170, 172. In particular, the guide plate 174 can be sufficiently short that it does not extend into the pharynx. In some embodiments, the guide plate 174 may be restricted to the hard palette region of the roof of the mouth, and may be configured so as not to trigger a pharyngeal or gag reflex in the patient.

Sidewalls 176, 178 can extend downwardly from the guide plate 174 at lateral sides of the bite block 108. Each sidewall 176, 178 may decrease in height in a rearward direction. For example, in the illustrated embodiment the sidewalls are substantially triangular. As can be seen in FIG. 5C, the sidewalls 176, 178 can angle inwardly in a rearward direction toward an imaginary vertically extending central longitudinal plane LP. In the illustrated embodiment, the guide plate 174 and the sidewalls 176, 178 angle inwardly at a large angle near the distal end 162 of the bite block 108, but define a more shallow angle at a position that is spaced from the distal end 162. The distal end 162 of the bite block 108 may be substantially pointed, although the tip thereof may be rounded so as to prevent trauma to the mouth of a patient.

A base plate 179 can extend rearwardly from the lower bite plate 172 and can border a lower end of the sidewalls 176, 178. The base plate 179 can be substantially shorter than the guide plate 174. The rearward edges of the base plate 179 and the sidewalls 176, 178 may be shaped to accommodate and/or rest against the tongue of a patient. In the illustrated embodiment, the base plate 179 is angled downwardly from the lower bite plate 172. In some embodiments, the base plate 179 can be configured to contact a tongue of a patient, and may hold down the tongue so as to prevent it from blocking a pathway through the oral cavity and into the pharynx.

The upward and downward angling of the guide plate 174 and the base plate 179, respectively, can assist in positioning the bite block 108 within the mouth of the patient. For example, the angled surfaces of the plates 174, 179 can urge teeth that clamp down against the plates toward the upper and lower bite plates 170, 172, respectively.

The guide plate 174 can include an entrance region 180 at a forward end of the guide plate 174 and an exit region 182 at a rearward end of the guide plate 174. In some embodiments, the sidewalls 176, 178 can border the guide plate 174 from the entrance region 180 to the exit region 182. The guide plate 174 and/or the sidewalls 176, 178 can be substantially funnel shaped. For example, the lower surface of the guide plate can funnel from the entrance region 180 to the exit region 182. The exit region 182 thus can define a smaller transverse width than does the entrance region 180.

The bite block 108 can be configured to constrain movement of a tip of a fiberscope or other elongated medical instrument that is advanced through the passageway 173 so as to cause the fiberscope to exit the bite block 108 at a position that is generally along and towards a midline of a patient. Such an arrangement can assist a practitioner in successfully locating the larynx and the trachea of the patient. For example, a distal tip of a fiberscope can be inserted into the passageway 173 and urged along the lower surface of the guide plate 174. Due to the curvature of the guide plate 174, the distal tip can be directed to a center line of the guide plate 174 (e.g., a line defined by the central longitudinal plane LP), which can be generally aligned with a midline of the patient. The fiberscope as whole may be aligned with the center line of the guide plate 174 and/or midline of the patient. The practitioner thus may be provided with useful information regarding a position of the distal tip of the fiberscope as it exits the bite block 108 and/or is advanced through the airway of a patient. The bite block 108 may also maintain the fiberscope generally aligned with the midline of the patient as the fiberscope is advanced through the airway. As maintenance of a fiberscope in alignment with the midline (e.g., in alignment with the central longitudinal plane LP) can be a major impediment to effective fiberoptic intubation of the trachea, bite blocks 108 that include features such as just described can be particularly useful in efficient and successful fiberoptic intubation of the trachea.

In the illustrated embodiment, the bite plate 108 is symmetrical about the longitudinal plane LP. Such an arrangement can be useful in conforming to a symmetrical anatomy of a patient, and may assist in centering a fiberscope.

Figure 5A:
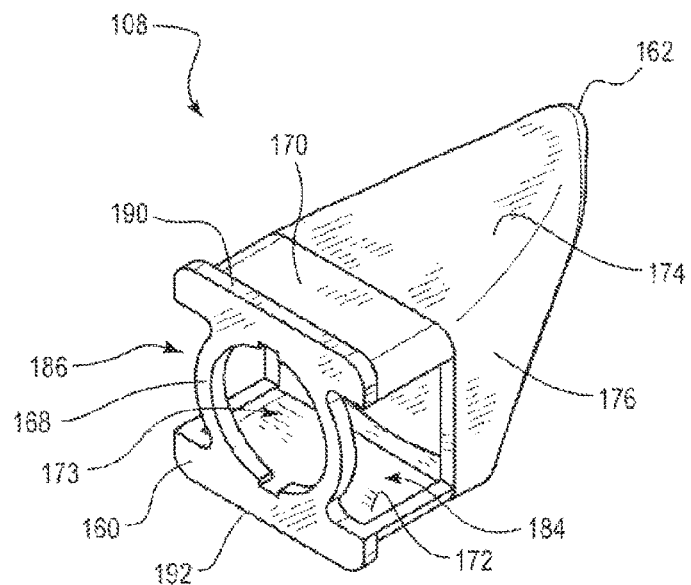
FIG. 5A is a front perspective view of the bite block of FIGS. 4A-4C.

As shown in FIG. 5A, the lateral sides of the bite block can include openings 184, 186 through which oxygen and/or other gases can escape without entering the mouth of a patient when the bite block 108 is secured in the mouth of the patient. The gases can be received into the cavity 156 of the mask 102, and may be inhaled through the nose of the patient.

Figure 5B:
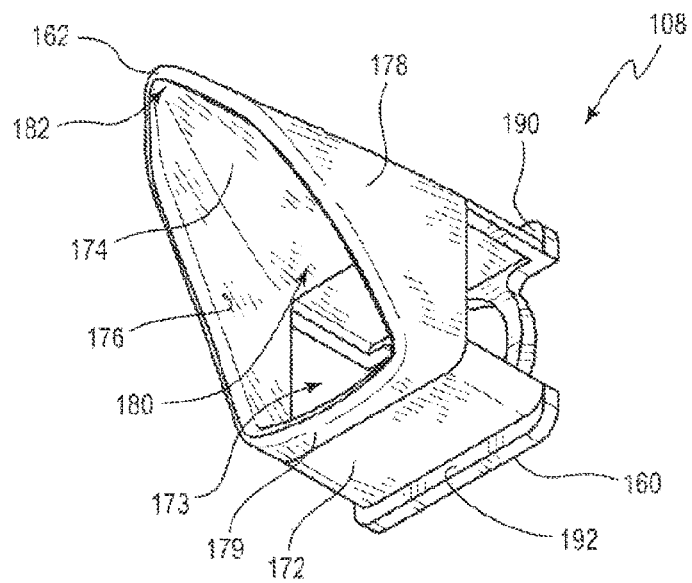
FIG. 5B is a rear perspective view thereof.
Figure 5C:
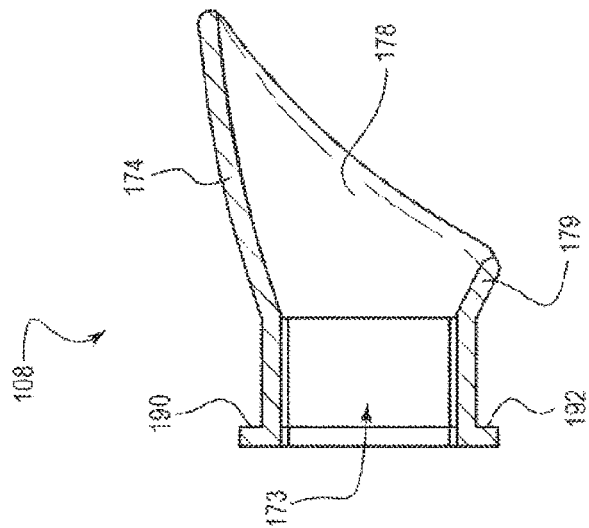
FIG. 5C is a bottom plan view thereof.
Figure 5D:
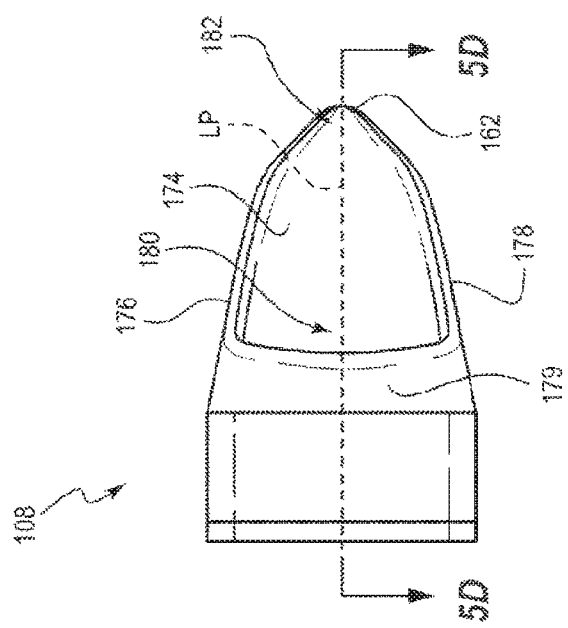
FIG. 5D is a cross-sectional view thereof taken along the view line 5D-5D in FIG. 5C.

With reference to FIGS. 5A, 5B, and 5D, the bite block 108 can include one or more stops 190, 192 that are configured to prevent the bite block 108 from being inserted past a desired position within the mouth of a patient. In the illustrated embodiment, the stops 190, 192 comprise flange portions that extend upwardly from the upper bite plate 170 and downwardly from the lower bite plate 172, respectively.

The bite block 108 can be configured to withstand biting by a patient so as to maintain the passageway 173 open. In some embodiments, the bite block 108 comprises a rigid or semi-rigid material, such as any suitable plastic material. In the illustrated embodiment, the openings 184, 186 can reduce the structural integrity of the bite block 108. The upper bite plate 170 and the lower bite plate 172 may be integral with or rigidly attached to the guide plate 174 and the base plate 179, respectively, such that large displacements of the bite plates 170, 172 are nevertheless prevented. The coupling ring 168 may also help to prevent large displacements of the bite plates 170, 172 under a compressive biting force of a patient.

Figure 6A:
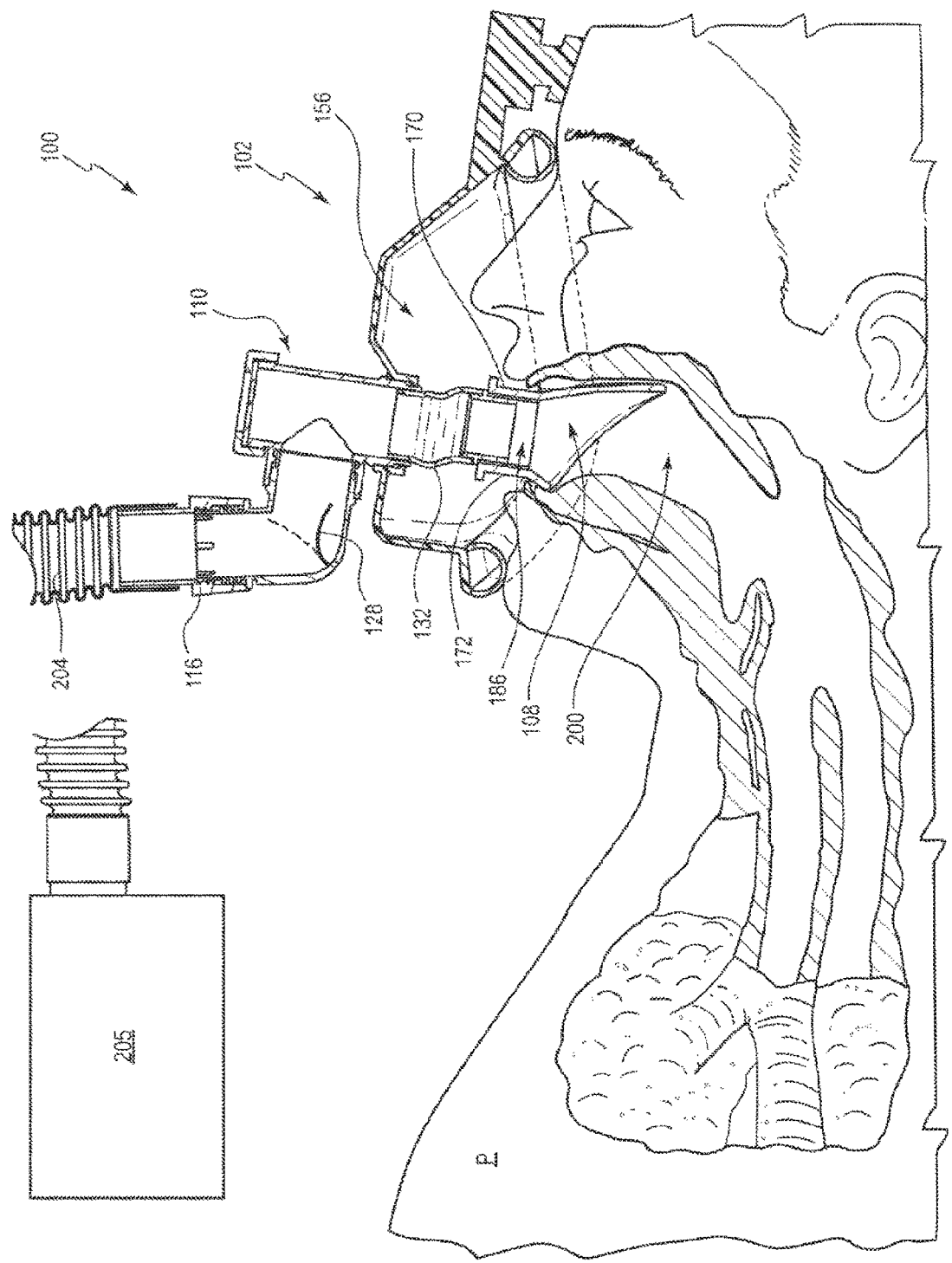

FIGS. 6A-6E depict various stages of an illustrative method of using the system 100 with a patient P. In many instances, the patient is permitted to remain fully awake or is only partially sedated while the method is carried out. With reference to FIG. 6A, the adapter 110, the conduit 132, and the bite block 108 may all be pre-coupled with the mask 102. The bite block 108 can be inserted into the oral cavity 200 of the patient P. The bite block 108 can be sized and dimensioned to be constrained within the oral cavity (e.g., to not extend into the pharynx or beyond) when the patient's teeth clamp against the bite plates 170, 172 of the bite block 108.

The bite block 108 can be repositioned relative to the mask 102 so as to have an appropriate fit within the oral cavity 200 while the mask 102 fits securely against the face of the patient P. In the illustrated embodiment, the conduit 132 is bent or displaced from a resting position to accommodate the repositioning of the bite block 108.

The connector 116 can be secured to any suitable interface of an assisted respiration source 205. In the illustrated embodiment, a corrugated tube 204 couples the assisted respiration source 205 to the connector 116. The assisted respiration source 205 can be configured to deliver oxygen, and optionally other gases (e.g., air) to the patient P. The gases can be unpressurized or pressurized, depending on the application. In some instances, the assisted respiration source 205 comprises any suitable ventilation machine, such as, for example, ventilation machines that are commonly used in NIPPV applications. Such NIPPV applications can include continuous positive airway pressure (CPAP) and/or variable or bilevel positive airway pressure (VPAP or BiPAP). In other or further instances, the assisted respiration source 205 may comprise a bag, which can be configured for use in bag valve mask ventilation procedures.

In the illustrated embodiment, pressurized air flows into the adapter 110 from the assisted respiration source 205, thereby opening the valve 128. The air is thus permitted to flow through the conduit 132 and through the bite block 108 into the airway of the patient P. Some air can exit from the bite block 108 through the side openings 184, 186 into the cavity 156 of the mask 102, and may thereafter be breathed in through the nose of the patient.

Figure 6B:
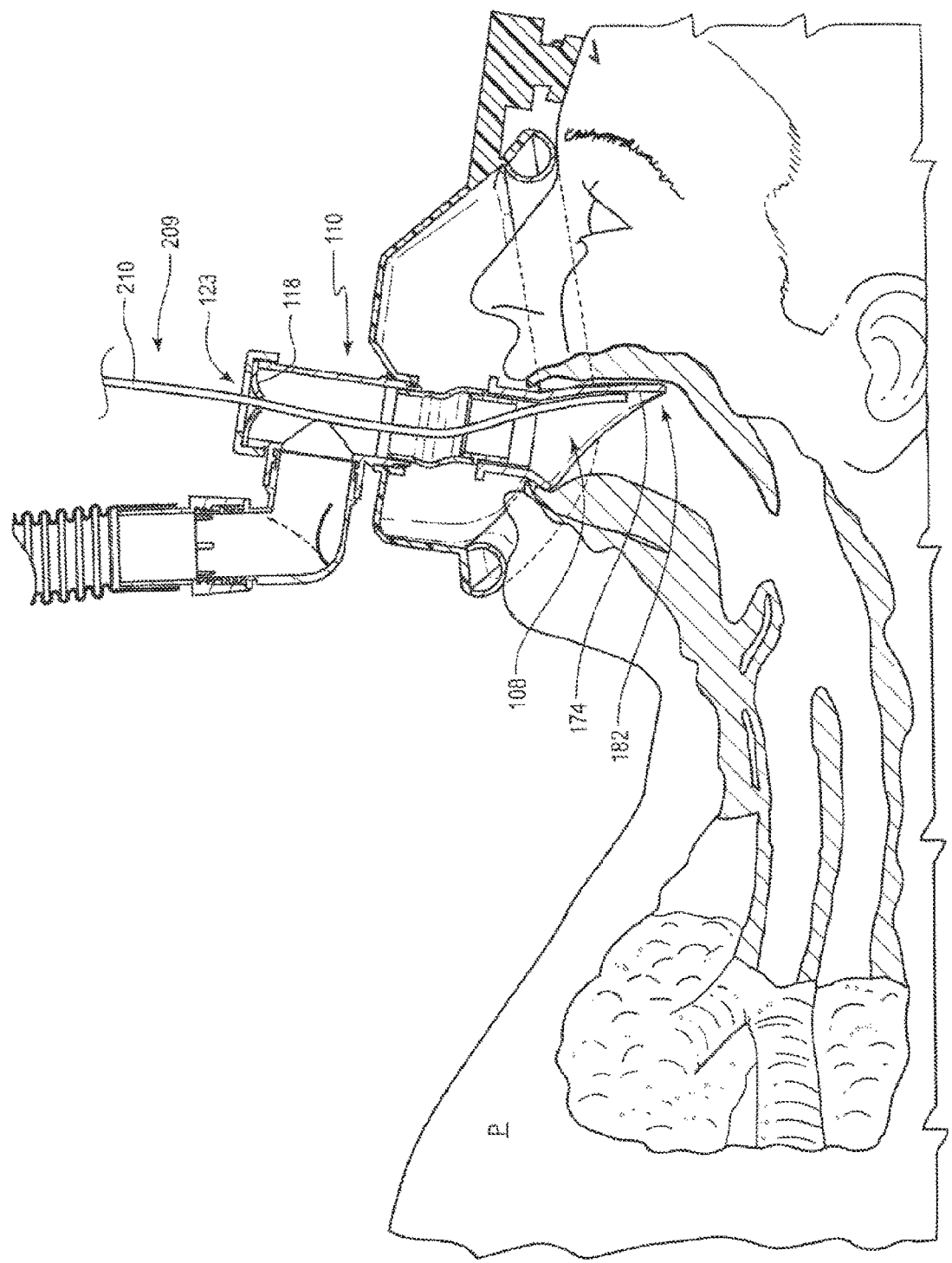

As shown in FIG. 6B, an elongated medical instrument 209 of any suitable variety can be inserted through the port 123 and through the bite block 108 into the airway of the patient P. In some instances, the medical instrument 209 can comprise any suitable device or probe, such as a fiberscope 210, a light wand, an intubating stylet, a fiberoptic intubating stylet, a specialized suction device, etc. As the fiberscope 210 is inserted through the port 123, the valve can maintain a seal therewith so as to prevent oxygen or air from exiting the adapter 110 thereat. A distal end of the fiberscope 210 can be advanced against the guide plate 174 of the bite block 108 and can be funneled toward the exit region 182 in a manner such as described above. The bite block 108 thus can assist in orienting the fiberscope 210 generally along a midline of the patient P. The fiberscope 210 can be thus manipulated from a position that is exterior to the mask 102.

Figure 6C:
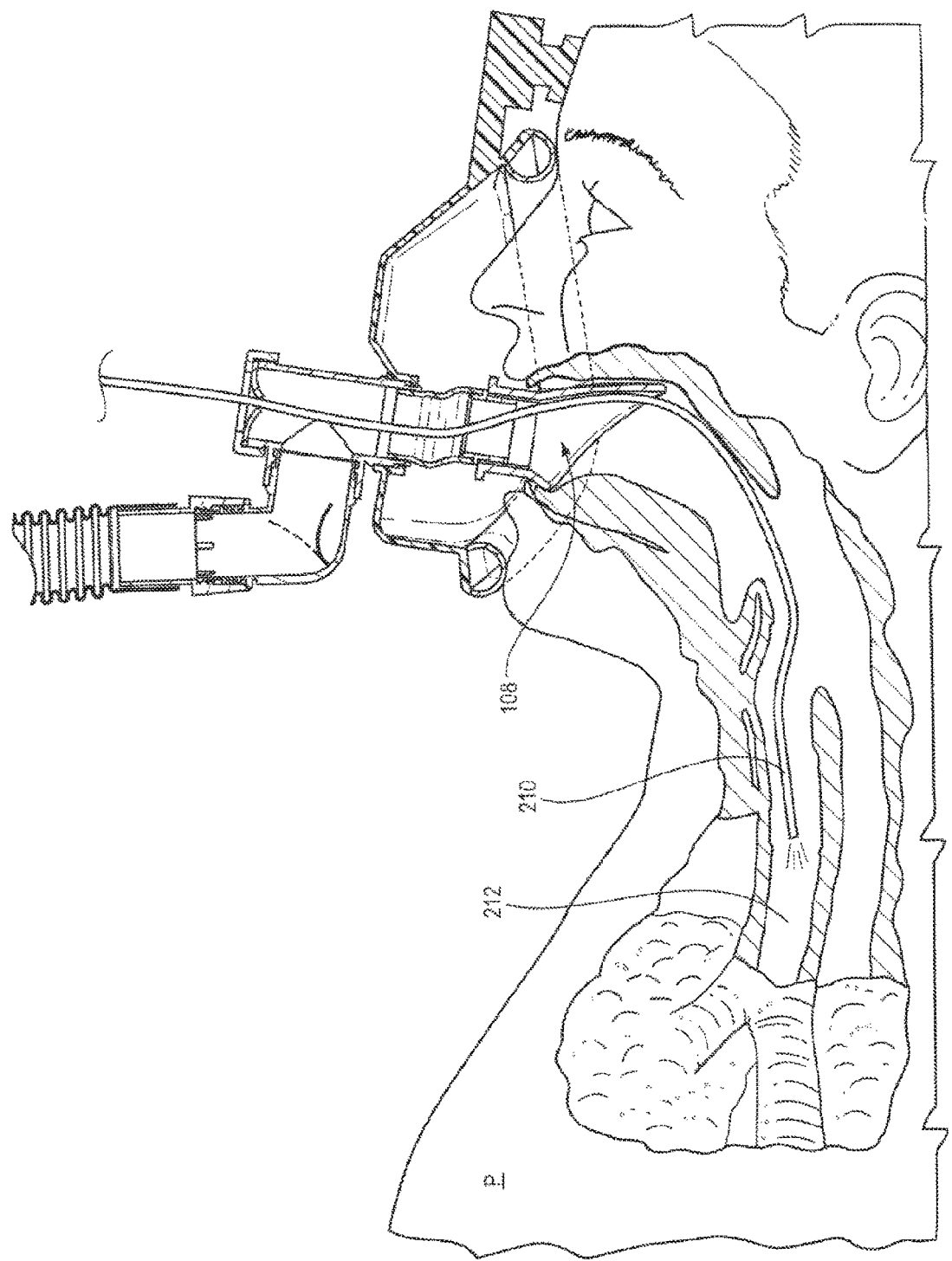

With reference to FIG. 6C, once the fiberscope 210 has been advanced past the distal end of the bite block 108, it can be advanced into the trachea 212 of the patient P. Various techniques for guiding a fiberscope 210 through the airway of a patient are known.

Figure 6D:
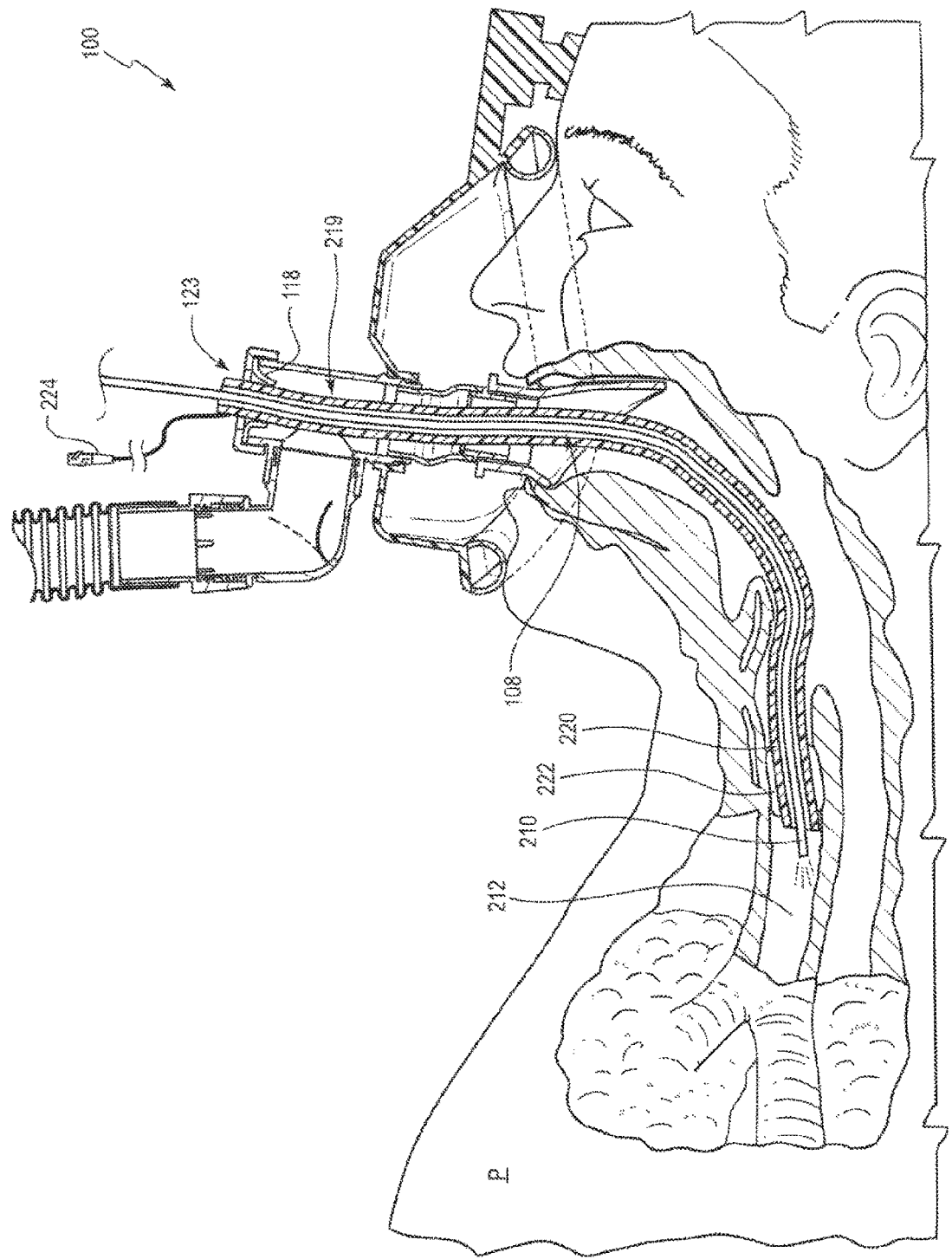

FIG. 6D illustrates that after the fiberscope 210 has been positioned as desired, another elongated medical instrument 219 can be inserted into the patient via the system 100. The medical instrument 219 can comprise any suitable cannula, such as an endotracheal tube 220. The endotracheal tube 220 can be advanced over the fiberscope 210 or similar medical instrument, through the insertion port 123, through the bite block 108, and into the trachea 212. The endotracheal tube 220 can be thus manipulated from a position exterior to the mask 102. The endotracheal tube 220 can cause greater deformation of the valve 118, which can substantially maintain a seal with the endotracheal tube 220. Once a distal end of the endotracheal tube 220 is in a desired position within the trachea 212, a balloon cuff 222 can be inflated via a port 224 to secure the endotracheal tube 220 in place in any suitable manner, such as those known in the art.

With reference to FIG. 6E, once the endotracheal tube 220 is positioned as desired and secured in place, the system 100 can be removed. In particular, the fiberscope 210 can be withdrawn through the endotracheal tube 220. The bite block 108 can be removed from the mouth of the patient P and the adapter 110, the mask 102, the conduit 132, and the bite block 108 can be withdrawn over a proximal end of the endotracheal tube 220. The proximal end of the endotracheal tube 220 can then be coupled with an assisted respiration source 205 (see FIG. 6A) in any suitable manner.

Figure 7:
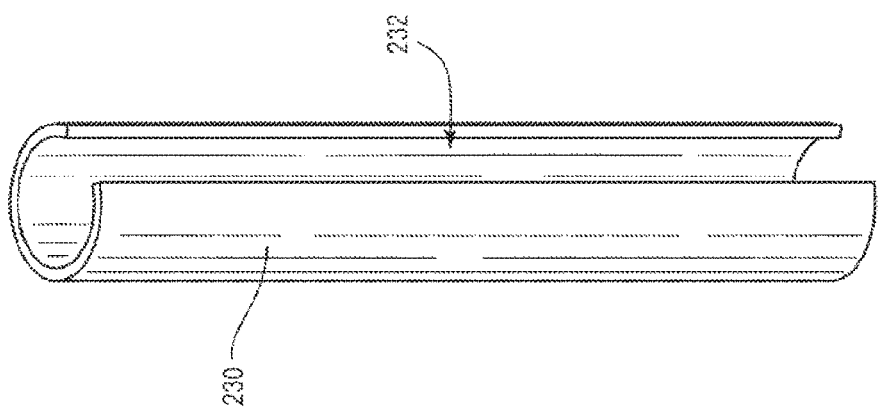
FIG. 7 is a perspective view of an embodiment of a pushing tube.
Figure 8A:
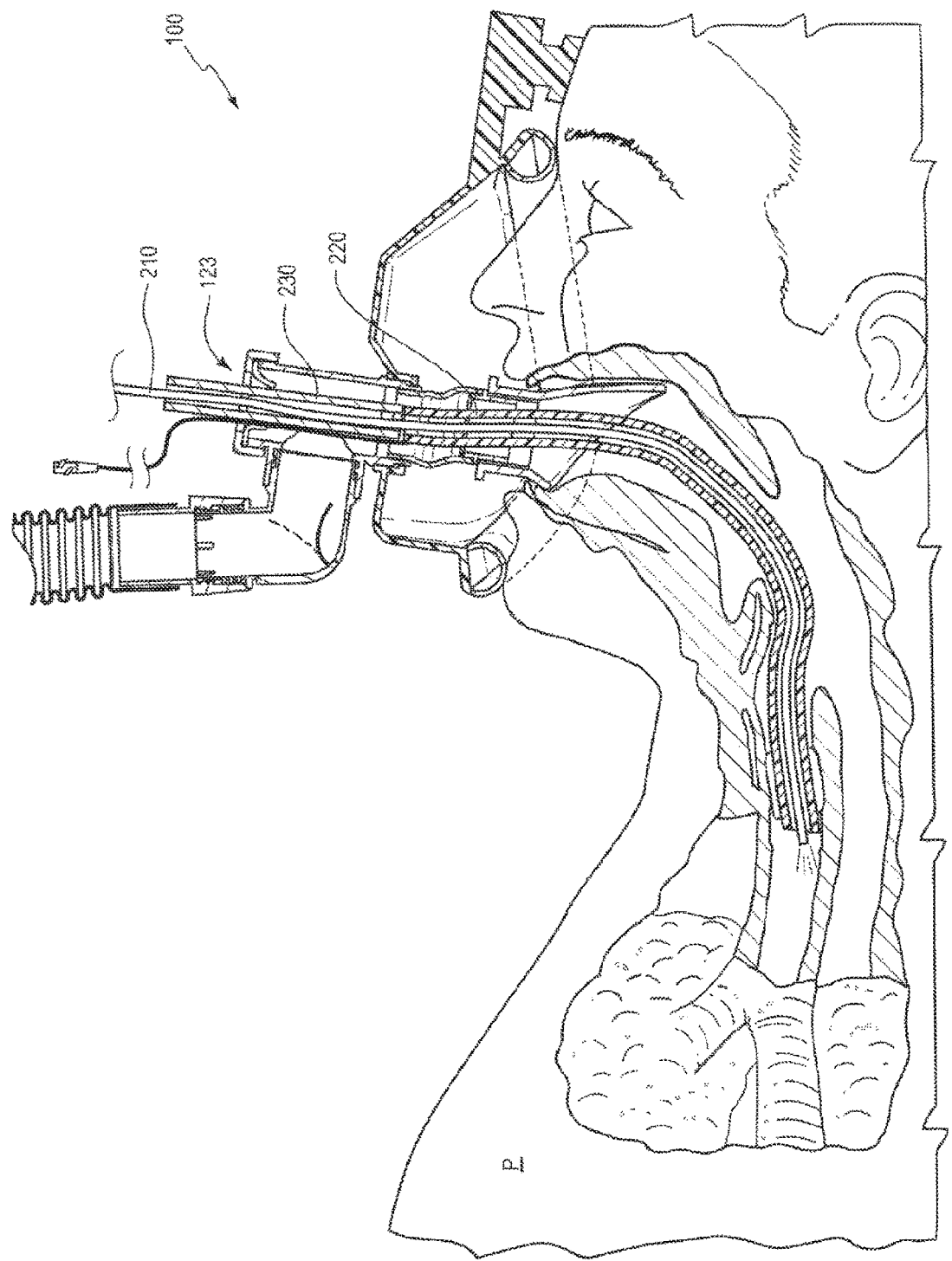
FIGS. 8A-8B are cross-sectional views of the system of FIG. 1 coupled with a patient that depict various stages of another intubation process such as that depicted in FIGS. 4A-4E that utilizes the pushing tube of FIG. 7.

FIGS. 7 and 8A illustrate a pusher 230 that can aid in using the system 100 with different patient anatomies, where an endotracheal tube 220 may have a fixed length. The pusher 230 can include a slit or opening 232 through which the pusher 230 can be placed over the fiberscope 210 or through which the fiberscope 210 may be inserted. As shown in FIG. 8A, In some instances, the system 100 may be used with a patient P who has a long neck, such that the endotracheal tube 220 might be advanced through the airway of the patient a greater distance in order to arrive at the desired position. The pusher 230 thus may be advanced through the insertion port 123 and over the fiberscope 210 so as to advance the endotracheal tube 220 to the desired position.

Figure 8B:
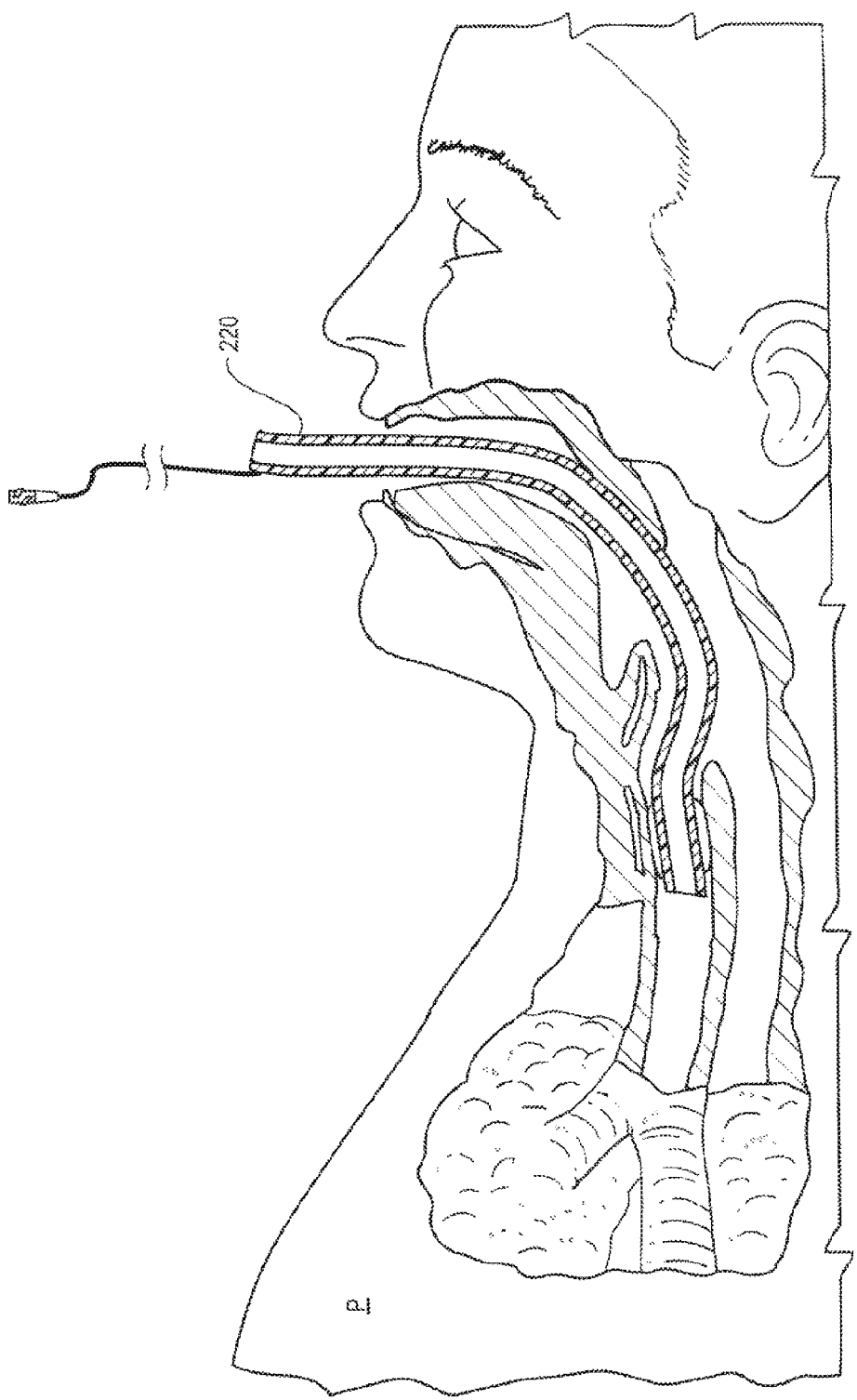

As shown in FIG. 8B, the pusher 230 may be removed along with the fiberscope 210 and the system 100, while leaving the endotracheal tube 220 in place. A proximal end of the endotracheal tube 200 may be positioned closer to the mouth of the patient in FIG. 8B than it is to the mouth of the patient in FIG. 6E.

The pusher 230 also can aid in using the system 100 with differently dimensioned endotracheal tubes. Certain endotracheal tubes are manufactured in different diametrical sizes and different lengths, but are designed for use with standard laryngoscope procedures. An endotracheal tube of this variety thus may be manipulated directly so as to position a distal end thereof only a short distance from the mouth of a patient once the tube is in place. The mask 102 and/or the insertion port 123 can prevent direct access to this region at which a distal end of such endotracheal tubes is typically positioned. Accordingly, the pusher 230 can allow for indirect access to the typical area at which the distal end of an endotracheal tube is positioned, and thus can assist in moving an endotracheal tube into its usual orientation relative to the patient. Such placement of the endotracheal tube can proceed while maintaining gas delivery to the patient without interruption, or substantially without interruption, and without removal of the mask 102.

Figure 9:
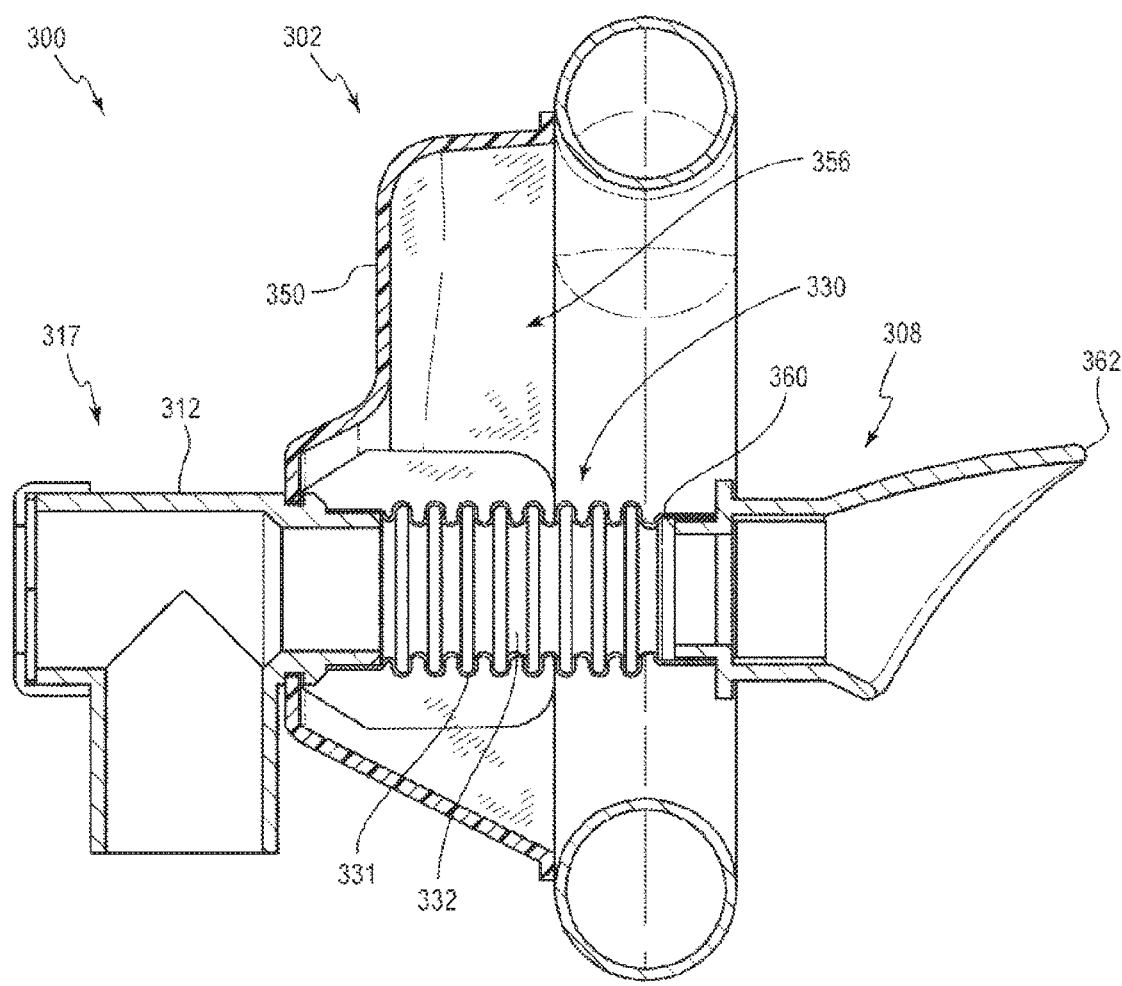
FIG. 9 is a cross-sectional view of another embodiment of a system that is configured for use in assisted respiration and in endotracheally intubating a patient.

FIG. 9 illustrates another embodiment of a system 300 that can resemble the system 100 described above in certain respects. Accordingly, like features are designated with like reference numerals, with the leading digits incremented to "3." Relevant disclosure set forth above regarding similarly identified features thus may not be repeated hereafter. Moreover, specific features of the system 300 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 300. Any suitable combination of the features and variations of the same described with respect to the system 100 can be employed with the system 300, and vice versa. This pattern of disclosure applies equally to further embodiments depicted in subsequent figures and described hereafter.

The system 300 includes a mask 302 that includes a shell 350. The mask 302 defines a cavity 356. An insertion assembly 317 that includes a housing member 312 can be coupled with the shell 350. The system 300 further includes a connection member 330, which consists of a flexible conduit 332. In the illustrated embodiment, the flexible conduit 332 comprises a corrugated tube having a series of outwardly extending rings 331. A proximal end of the connection member 330 is directly coupled with the housing member 312, and a distal end of the connection member 330 is directly coupled with a bite block 308. A proximal end 360 of the bite block 360 is positioned within the cavity 356 of the shell 350 when the system 300 is in a pre-use state, whereas a distal end 362 of the bite block 360 is at a position exterior to the cavity 356.

Figure 10A:
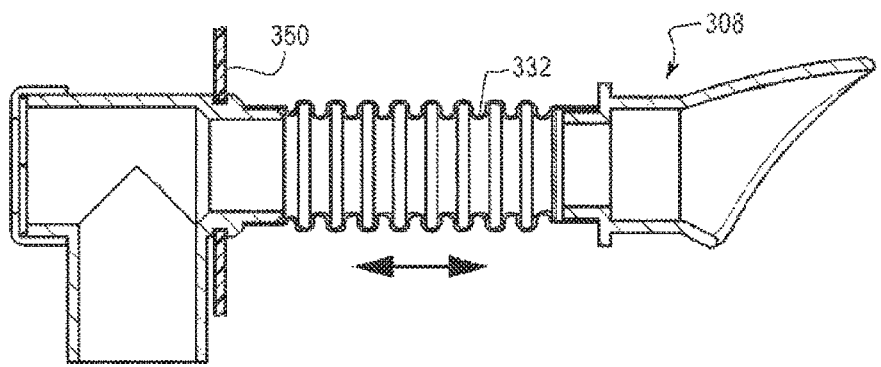
FIGS. 10A-10C are cross-sectional views of a portion of the system of FIG. 9 showing an embodiment of a bite block in a variety of different positions.
Figure 10B:
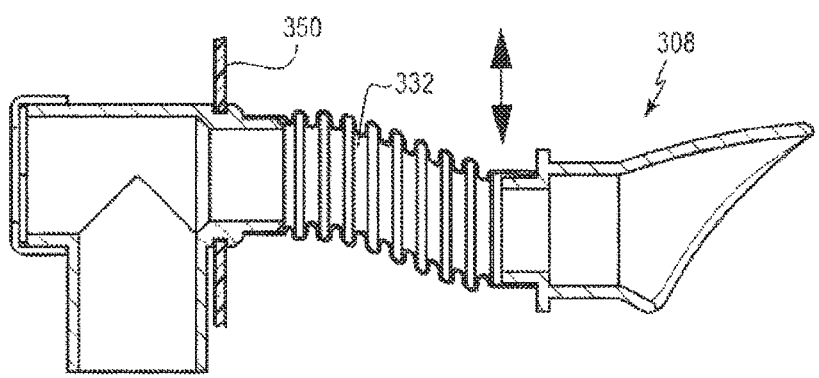
Figure 10C:
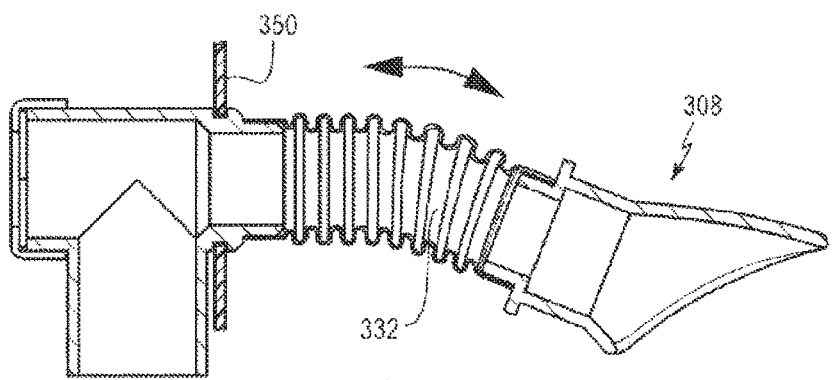

As shown in FIGS. 10A-10C, the bite block 308 can be moveable or adjustable relative to the shell 350, such that the system 300 can readily accommodate differing patient anatomies. FIG. 10A illustrates that the flexible conduit 332 can be extendible and/or compressible in a longitudinal direction, such that the bite block 308 can move directly away from or toward the shell 350. FIG. 10B illustrates that the flexible conduit 332 can permit the bite block 308 to move laterally relative to the shell 350. FIG. 10C illustrates that the flexible conduit 332 can permit rotation of the bite block 308 relative to the shell 350 about an axis other than a longitudinal axis through the flexible conduit 332. Although not depicted by arrows, the flexible conduit may further permit slight rotation of the bite block 308 about a longitudinal axis of the conduit 332 (e.g., the flexible conduit 332 may be configured to twist).

Figure 11A:
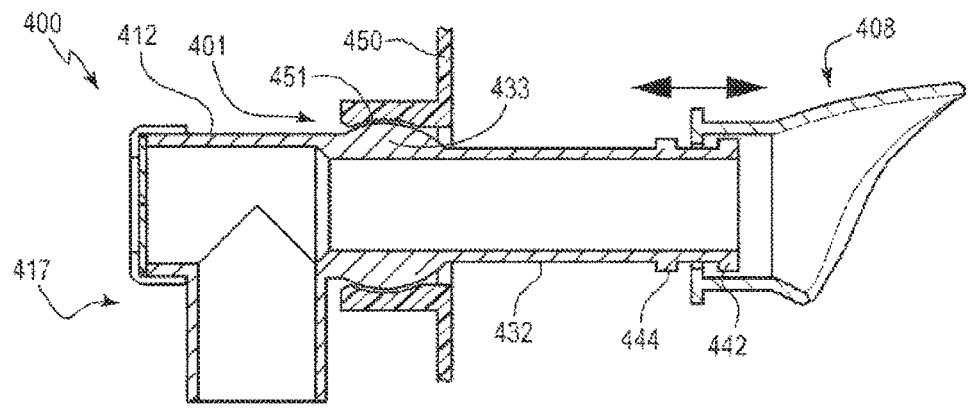
FIGS. 11A-11C are cross-sectional views of a portion of another embodiment of a system that is configured for use in assisted respiration and in intubating a patient showing an embodiment of a bite block in a variety of different positions.
Figure 11B:
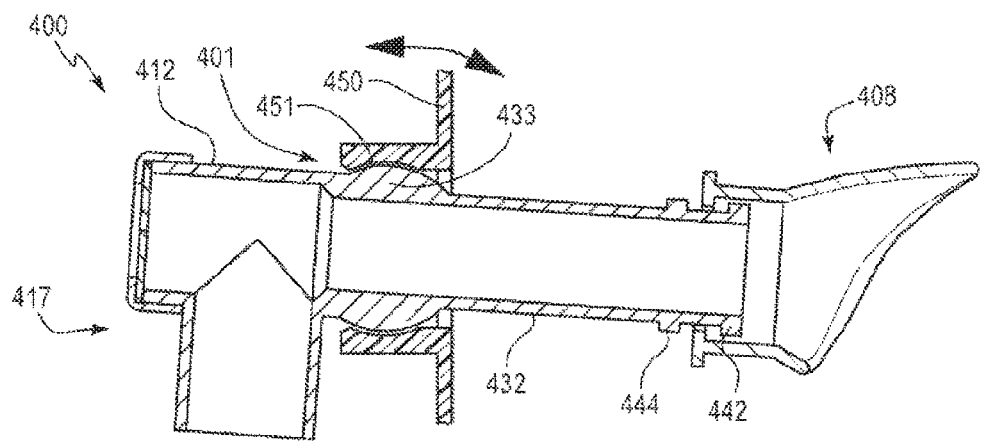
Figure 11C:
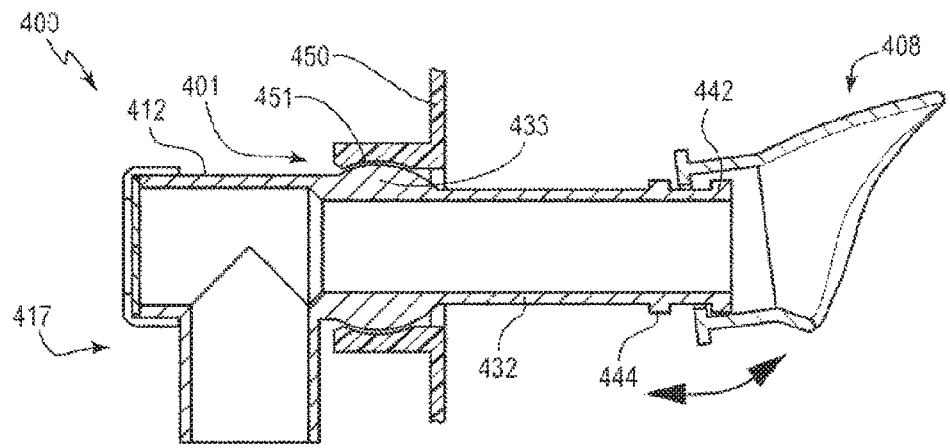

FIGS. 11A-11C illustrate another embodiment of a system 400 in which a bite block 408 has multiple degrees of freedom of movement relative to a shell 450 portion of a mask. An insertion assembly 417 can include a housing member 412. The housing member 412 can define a conduit 432. In some embodiments, the housing member 412 is rigid or semi-rigid, and the conduit 432 thus may be rigid or semi-rigid and can resist being bent or deformed. The housing member 412 can be connected to the shell 450 at a connection interface 401, which comprises a ball-and-socket joint in the illustrated embodiment. In particular, the housing member 412 includes a substantially spherically shaped protrusion that is configured to rotate within a substantially spherically shaped casing 451 defined by the shell 450.

As shown in FIG. 11A, the housing member 412 can define a forward stop 444 and a rearward stop 442 at a distal region of the conduit 432. The bite block 408 can move longitudinally between the stops 442, 444. As shown in FIG. 11B, the conduit 432, and hence the bite block 408, can rotate relative to the shell 450. In some instances, the rotation can be about axes other than a longitudinal axis of the conduit 432. In other or further instances, the rotation can be about the longitudinal axis. For example, the housing member 412 can be configured to rotate about its longitudinal axis within the shell 450 and/or the bite block 408 can be configured to rotate relative to the conduit 432 about the longitudinal axis. As shown in FIG. 11C, in some embodiments, the bite block 408 may fit loosely at the end of the conduit 432 and may be configured to rotate relative thereto.

Figure 12:
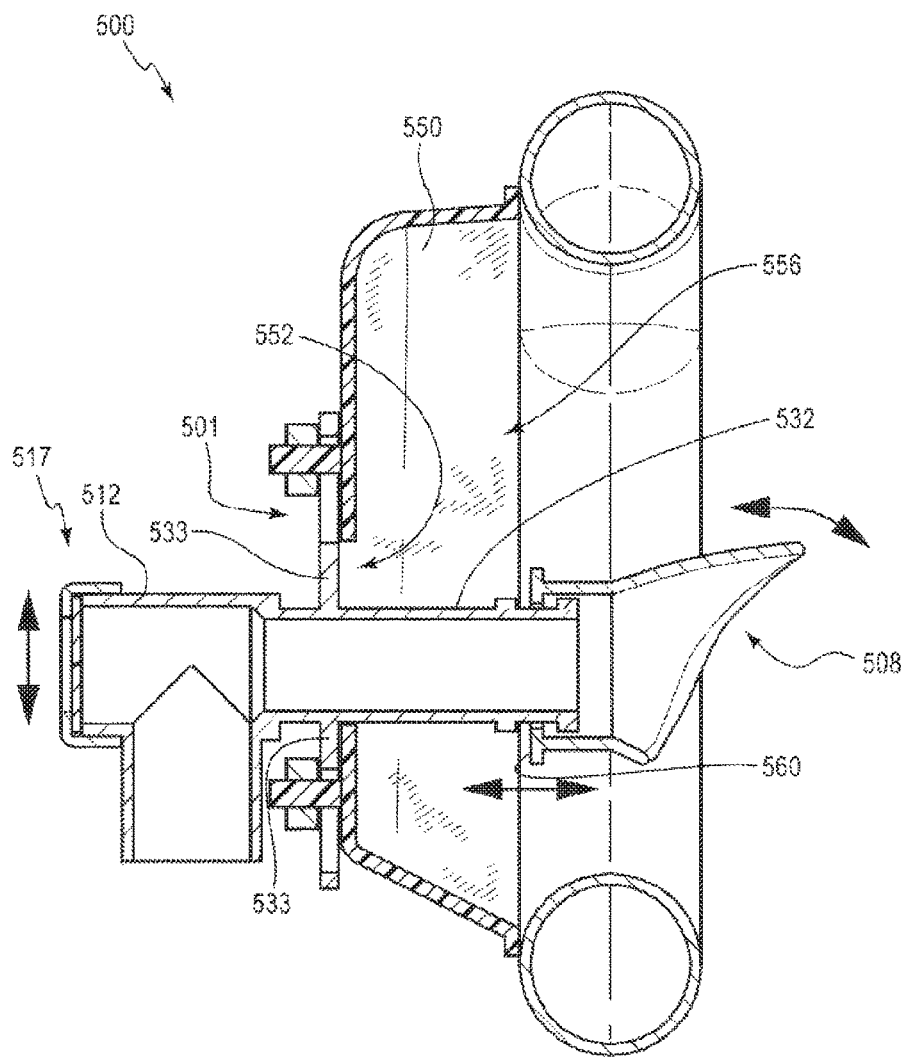
FIG. 12 is a cross-sectional view of another embodiment of a system that is configured for use in assisted respiration and in intubating a patient.

FIG. 12 illustrates another embodiment of a system 500, which includes a shell 550, which defines an adapter opening 552 and at least a portion of a cavity 556, and a bite block 508 that is capable of being adjusted relative to the shell 500. An insertion assembly 517 can include a housing member 512 that defines a conduit 532 similar to the conduit 432 described above. The housing member 512 can be connected to the shell 550 at a connection interface 501. In the illustrated embodiment, the connection interface 501 is configured to permit the housing member 512 to slide relative to the shell 550. The housing member 512 can include one or more flanges 533 that are configured to block or close the adapter opening 552 of the shell 550 regardless of the position to which the housing member 512 is slid relative to the shell 550. As shown by the double-headed arrows, the bite block 508 can have multiple degrees of freedom of movement relative to the shell 550.

FIGS. 13A-13D illustrate another embodiment of a bite block 608 that can resemble the bite block 108 described above. The bite block 608 can include features that assist in orientation and/or advancement of medical instruments into the airway of a patient. The bite block 608 can include an upper bite plate 670 and a lower bite plate 672 that are substantially rectangular and planar, although other suitable configurations are also possible. The upper and lower bite plates 670, 672 cooperate to define a forward end of passageway 673 through which an elongated medical instrument may pass. The passageway 673 can be devoid of a coupling ring, such as the coupling ring 168 described above, such that a forward end of the passageway 673 may be larger than a forward end of the passageway 173 described above.

Figure 13B:
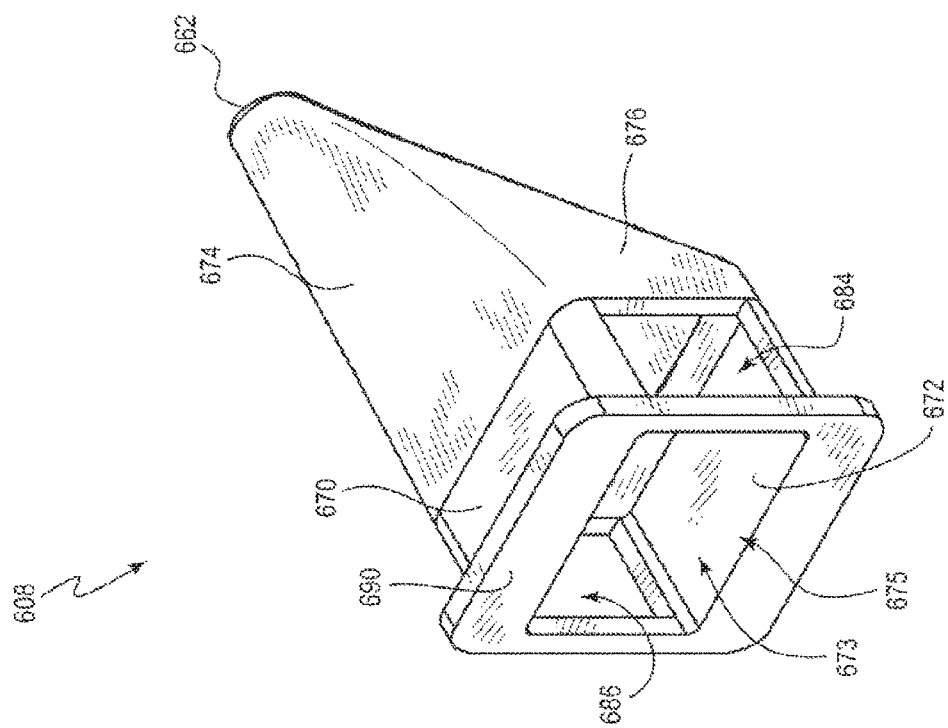
FIG. 13B is a rear perspective view thereof.
Figure 13A:
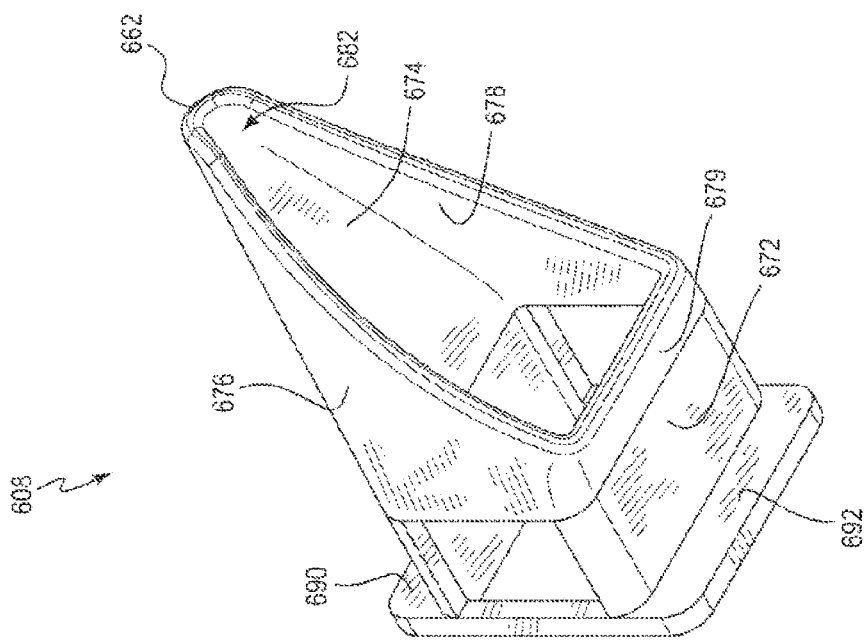
FIG. 13A is a front perspective view of another embodiment of a bite block.
Figure 13D:
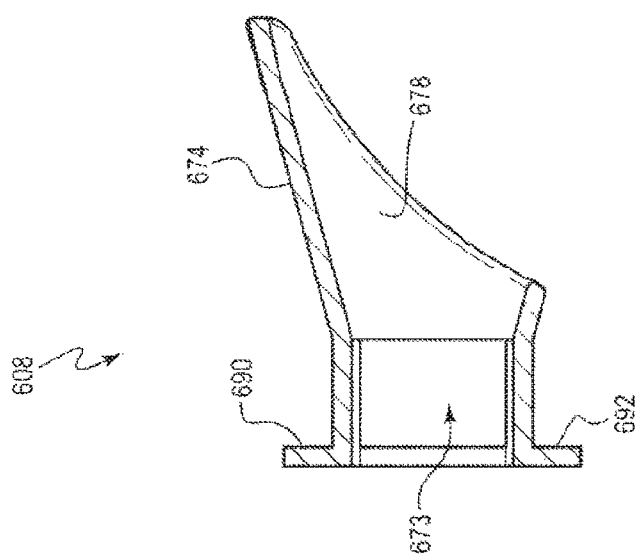
FIG. 13D is a cross-sectional view thereof taken along the view line 13D-13D in FIG. 13C.
Figure 13C:
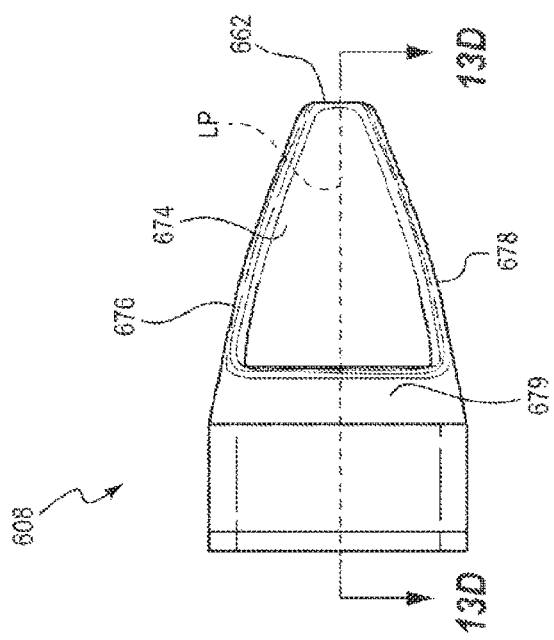
FIG. 13C is a bottom plan view thereof.

The bite block 608 can include a guide plate 674, sidewalls 676, 678, and a base wall 679. As shown in FIG. 13C, the sidewalls 676, 678 may taper gradually inward toward a central longitudinal plane LP of the bite block 608. A distal end 662 of the bite block 608 can be substantially flat. The bite block 608 can include lateral openings 684, 686 and upper and lower stops 690, 692 such as similarly numbered features discussed above.

FIG. 14 illustrates another embodiment of a bite block 708 that can resemble the bite blocks 108, 608 described above. The bite block 708 can be configured for use in altering a configuration of a mask portion of a system. For example, the bite block 708 can be used in retrofitting a mask and/or can be inserted through an opening in the mask without removing the mask from a patient, as discussed further below.

The bite block 708 can include an upper bite landing or plate 770 (see FIG. 15C) and a lower bite landing or plate 772. The upper and lower bite plates 770, 772 are substantially rectangular and planar, although other suitable configurations are also possible. The upper and lower bite plates 770, 772 can be formed as recesses in a body 771, which is shaped substantially cylindrically in the illustrated embodiment.

The body 771 can define a guide plate 774, sidewalls 776, 778, and a base wall 779, which may smoothly transition from one to another. The sidewalls 776, 778 can define one or more lateral openings 784, 786. An inner surface of the body can be concavely rounded and can assist in centering a fiberscope in manners such as discussed above. An outer diameter of the bite block 708 can be sufficiently small to permit the bite block 708 to pass through an adapter opening of a mask, as discussed hereafter.

Figure 15B:
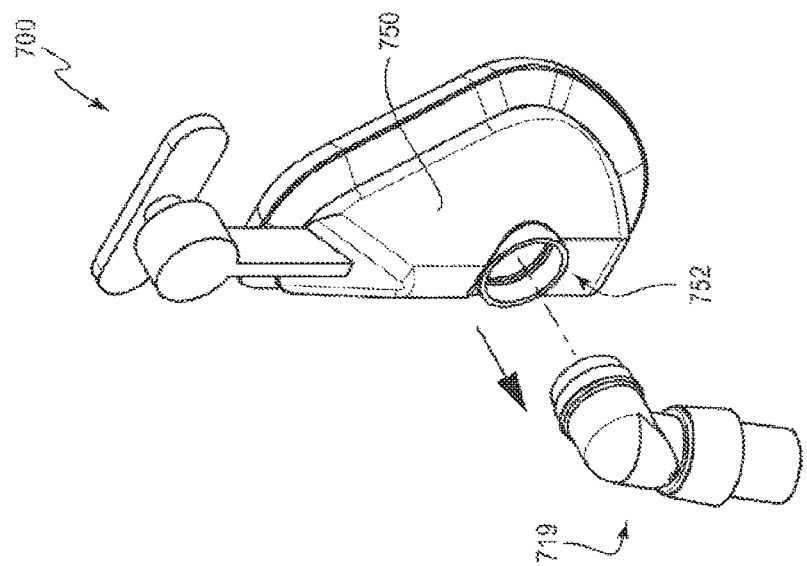

FIGS. 15A-15D illustrate a system 700 such as the systems discussed above, and depict various stages of an illustrative method of adjusting or retrofitting a mask 702. The mask 702 can include a shell 750 that defines an adapter opening 752 (FIG. 15B).

Figure 15A:
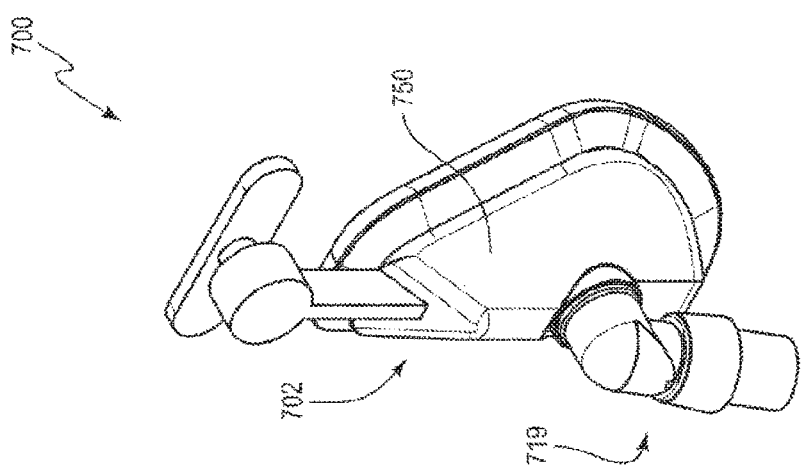

As shown in FIG. 15A, an assisted respiration source assembly 719 can initially be coupled with the mask 702 at the adapter opening 752. The assisted respiration source assembly 719 can resemble the assisted respiration source assembly 119 discussed above, and can be configured to deliver oxygen and optionally additional gases to the patient via the mask 702. However, the assisted respiration source assembly 719 can be devoid of features that would permit the insertion of medical devices through the adapter opening 752.

As shown in FIG. 15B, the assisted respiration source assembly 719 can be removed from the mask 702. For example, if it is determined that a medical instrument should be delivered to the airway of the patient, the assisted respiration source assembly 719 can be removed so as to expose the adapter opening 752.

As shown in FIG. 15C, an insertion assembly 717 can be coupled with the mask 702 at the adapter opening 752. The insertion assembly 717 can be coupled with a connection member 730, such as a flexible conduit 732, which can in turn be coupled with the bite block 708. The bite block 708 and the flexible conduit 732 can be advanced through the adapter opening 752, and the insertion assembly 717 can be coupled with the mask 702. In some embodiments, the assisted respiration source assembly 719 can be attached to the insertion assembly 717.

As shown in FIG. 15D, the coupled insertion assembly 717 and assisted respiration source assembly 719 can cooperate as an adapter 710, such as the adapter 110 discussed above. One or more elongated medical devices can be inserted through the insertion assembly 717 in manners such as discussed above with respect to the insertion assembly 117. In some instances, the insertion assembly 717 may be used without the conduit 730 and/or without the bite block 708.

In some instances, the adaptation, retrofitting, or adjustment of the mask 702 can take place prior to placement of the mask 702 on the patient. In other instances, the adjustment can take place while the patient is wearing the mask 702.

As previously mentioned, while the drawings and written description have focused on illustrative devices, systems, and methods related to the placement of an endotracheal tube, it is to be understood that embodiments may be used in any other suitable context, such as contexts where other elongated medical instruments are inserted into an airway of the patient when it is desirable to provide assisted respiration to the patient. In some instances, embodiments may be used with procedures that enter the esophagus or stomach. Accordingly, in various embodiments, elongated medical instruments may be inserted into upper and/or lower aerodigestive tracts.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Embodiments of the invention in which an exclusive property or privilege is claimed are defined as follows.

The invention claimed is:

1. A method for accessing a mouth of a patient during assisted respiration, the method comprising:
   coupling a non-invasive positive pressure ventilation (NIPPV) mask on a patient, wherein the NIPPV mask defines a cavity configured to encompass a mouth of the patient and operate under positive pressure, wherein the NIPPV mask comprises a shell that defines an adapter opening, wherein the NIPPV mask is coupled to the patient via an attachment assembly including one or more straps configured to couple with a head of the patient and configured to couple the NIPPV mask with a face of the patient and hold the NIPPV mask on the face when positive pressure is applied to the NIPPV mask;
   decoupling a first adapter from direct coupling with the adapter opening of the NIPPV mask after the NIPPV mask has been coupled with the face of the patient; and
   coupling a second adapter with the adapter opening of the NIPPV mask after the NIPPV mask has been coupled with the face of the patient and after the step of decoupling the first adapter, the second adapter having a first passageway configured to extend between a first valve that is in communication with an exterior of the second adapter and the adapter opening of the NIPPV mask when the second adapter is coupled with the adapter opening, wherein the first valve comprises a septum that includes one or more slits and is configured to permit passage, along a linear pathway, of a distal end of at least one elongated instrument into the mouth of the patient, wherein the second adapter further comprises a second passageway configured to receive gas from an NIPPV ventilator, a central axis of the second passageway being axially offset from, and forms an acute or perpendicular angle with, a central axis of the first passageway, wherein the second passageway comprises a second valve in communication with the second passageway, an entirety of the second valve being disposed between a proximal end and a distal end of the second passageway.

2. The method of claim 1, further comprising:
   coupling the NIPPV ventilator to the second adapter.

3. The method of claim 1, wherein a peripheral edge of the second valve is fixedly coupled to a sidewall of the second passageway.

4. The method of claim 1, wherein the first adapter is configured to receive gas from an NIPPV ventilator and permit the gas to pass through the adapter opening of the NIPPV mask prior to being decoupled from the adapter opening.

5. The method of claim 4, wherein the first adapter does not permit insertion of an elongate instrument through the first adapter and into the mouth of the patient.

6. The method of claim 1, further comprising:
   inserting the distal end of at least one elongated instrument into the mouth of the patient through the one or more slits of the septum.

7. A method for accessing a mouth of a patient during assisted respiration, the method comprising:
   obtaining a non-invasive positive pressure ventilation (NIPPV) mask, wherein the NIPPV mask defines a cavity configured to encompass a mouth of the patient and operate under positive pressure, wherein the NIPPV mask comprises a shell that defines an adapter opening, wherein the NIPPV mask is configured to be coupled to a patient via an attachment assembly including one or more straps configured to couple with a head of the patient and configured to couple the NIPPV mask with a face of the patient and hold the NIPPV mask on the face when positive pressure is applied to the NIPPV mask;

decoupling a first adapter from direct coupling with the adapter opening of the NIPPV mask, wherein the first adapter is configured to receive gas from an NIPPV ventilator and permit the gas to pass through the adapter opening of the NIPPV mask prior to being decoupled from the adapter opening;

coupling a second adapter with the adapter opening of the NIPPV mask after the step of decoupling the first adapter, the second adapter having a first passageway configured to extend between a first valve that is in communication with an exterior of the second adapter and the adapter opening of the NIPPV mask when the second adapter is coupled with the adapter opening, wherein the first valve comprises a septum that includes one or more slits and is configured to permit passage, along a linear pathway, of a distal end of at least one elongated instrument into the mouth of the patient, wherein the second adapter further comprises a second passageway configured to receive gas from an NIPPV ventilator, a central axis of the second passageway being axially offset from, and forms an acute or perpendicular angle with, a central axis of the first passageway, wherein the second passageway is in fluid communication with the first passageway to permit the gas to pass through the adapter opening of the NIPPV mask, wherein the second adapter comprises a second valve in communication with the second passageway, wherein an entirety of the second valve is disposed between a proximal end and a distal end of the second passageway; and coupling the NIPPV mask comprising the second adapter onto a patient.

8. The method of claim 7, further comprising:
inserting the distal end of at least one elongated instrument into the mouth of the patient through the one or more slits of the septum.

9. The method of claim 7, further comprising:
coupling the NIPPV ventilator to the second adapter.

10. The method of claim 7, wherein a peripheral edge of the second valve is fixedly coupled to a sidewall of the second passageway.

11. The method of claim 7, wherein the first adapter does not permit insertion of an elongate instrument through the first adapter and into the mouth of the patient.

* * * * *